United States Patent
Ascher et al.

Patent Number: 6,093,813
Date of Patent: *Jul. 25, 2000

[54] CEPHALOSPORIN COMPOUNDS

[75] Inventors: Gerd Ascher, Kundl; Johannes Ludescher, Breitenbach; Hubert Sturm, Innsbruck; Josef Wieser, Kufstein, all of Austria

[73] Assignee: Biochemie Gesellschaft m.b.H., Austria

[*] Notice: This patent issued on a continued prosecution application filed under 37 CFR 1.53(d), and is subject to the twenty year patent term provisions of 35 U.S.C. 154(a)(2).

[21] Appl. No.: 09/163,660

[22] Filed: Sep. 30, 1998

Related U.S. Application Data

[62] Division of application No. 08/732,501, Oct. 23, 1996, Pat. No. 5,856,474.

[30] Foreign Application Priority Data

| Apr. 25, 1994 | [AT] | Austria | 857/94 |
| Apr. 25, 1994 | [AT] | Austria | 858/94 |
| May 25, 1994 | [AT] | Austria | 1066/94 |

[51] Int. Cl.⁷ ............ C07D 501/18; C07D 501/04
[52] U.S. Cl. ............................. 540/217; 540/215
[58] Field of Search ................. 540/217; 544/2

[56] References Cited

U.S. PATENT DOCUMENTS

| 3,351,596 | 11/1967 | Chamberlin | 260/243 |
| 3,880,851 | 4/1975 | Webber | 424/246 |
| 3,984,401 | 10/1976 | Terao et al. | 260/243 C |
| 3,987,039 | 10/1976 | Yoshioka et al. | 260/243 C |
| 3,997,528 | 12/1976 | Yoshioka et al. | 424/246 |
| 4,101,658 | 7/1978 | Yoshioka et al. | 544/16 |
| 4,147,863 | 4/1979 | Miyadera et al. | 542/436 |

FOREIGN PATENT DOCUMENTS

| 0359536 | 9/1989 | European Pat. Off. |
| 0445821 | 3/1991 | European Pat. Off. |
| 05034539 | 9/1992 | European Pat. Off. |
| 05974295 | 5/1994 | European Pat. Off. |
| 2128605 | 6/1970 | Germany |
| 2538801 | 3/1976 | Germany |
| 50071691 | 11/1973 | Japan |
| 556876 | 10/1974 | Switzerland |
| 1356437 | 6/1971 | United Kingdom |
| 1447959 | 2/1975 | United Kingdom |

OTHER PUBLICATIONS

Sugawara, Tohru et al. Chemical & Pharmaceutical Bulletin, vol. 28, no. 4, Apr.. 1980, pp. 1339–1341.
Peter, Heinrich et al., Helvetica Chimica Acta, vol. 57, No. 7, 1974, pp. 2044–2054.
Cephalosporins & Penicillins, Chemistry & Biology, Ed. E. H. Flynn, Academic Press N.Y. & London, 1972, p. 166.
Hashimoto, T. et al., Chem. Pharm. Bull, 26 (6), 1978, pp. 1803–1811.
Bateson, J.H. et al., Bioorg. Chem. Let. 3, 1993, pp. 2219–2224.
Fieser and Fieser, Reagents for Organic Synthesis, John Wiley and Sons, Inc., 1967, p. 775.

*Primary Examiner*—Mukund J. Shah
*Assistant Examiner*—Pavanaram K Sripada
*Attorney, Agent, or Firm*—Lydia T. McNally; Stephen G. Kalinchak

[57] ABSTRACT

Cephalosporin derivatives of formula II

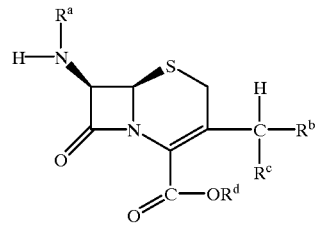

wherein $R^a$ denotes hydrogen or a silyl group; $R^b$ denotes a group of formula $-OR^e$, wherein $R^e$ denotes hydrogen or alkyl; and $R^c$ and $R^d$ together denote a bond; in free form or in salt form.

22 Claims, No Drawings

CEPHALOSPORIN COMPOUNDS

This application is a divisional of Ser. No. 08/732,501, filed Oct. 23, 1996, now U.S. Pat. No. 5,856,474, which is a 371 of PCT/EP95/01538, filed Apr. 24, 1994.

This invention relates to new intermediates in the preparation of cephalosporins.

Particularly it relates to a compound of formula

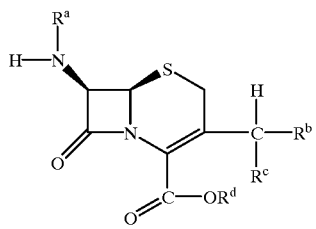

IA wherein either

α) $R^a$ denotes hydrogen or a silyl group; $R^b$ denotes a group of formula —$OR^e$, wherein $R^e$ denotes hydrogen or alkyl; and $R^c$ and $R^d$ together denote a bond; or β) $R^a$ and $R^d$ denote hydrogen or a silyl group; and $R^b$ and $R^c$ together denote an imino group of formula=N—Y, wherein Y denotes alkyl, aryl or heterocyclyl; or γ) $R^d$ denotes hydrogen or a silyl group; $R^a$ denotes hydrogen, if $R^d$ denotes hydrogen; or, $R^a$ denotes hydrogen or a silyl group, if $R^d$ denotes a silyl group; and $R^b$ and $R^c$ together denote the oxo group;

in free form or in salt form.

In one particular aspect the invention relates to a compound of formula

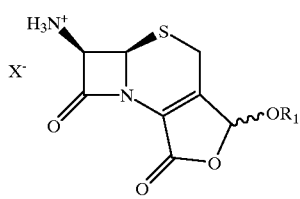

I wherein $X^{31}$ denotes the anion of an inorganic or organic acid and $R_1$ denotes hydrogen or an alkyl group.

In another particular aspect the invention relates to a compound of formula

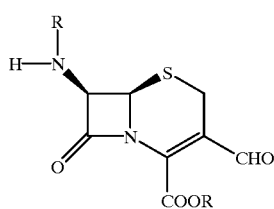

Ia wherein R denotes hydrogen or a silyl group.

In another particular aspect the invention relates to a compound of formula

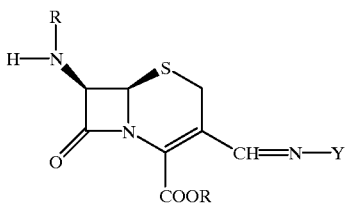

II wherein Y and R are as defined above in free form or salt form.

Alkyl, aryl or heterocyclyl in the meaning of Y include unsubstituted alkyl, aryl or heterocyclyl; or, by amino, dialkylamino, hydroxy, alkoxy, alkyl, aryl, nitro, halogen, carbalkoxy or carbamido substituted alkyl, aryl or heterocyclyl. Y denotes preferably tert.-butyl, phenyl, naphthyl or pyrimidinyl.

If not otherwise stated herein alkyl includes an alkyl group having 1 to 22, for example 1 to 12, such as 1 to 8 carbon atoms, preferably lower alkyl, such as ($C_{1-4}$)alkyl. An alkyl group may be unsubstituted or substituted by groups which are inert under relevant reaction conditions. A silyl group is preferably a silyl protecting group and includes a conventional silyl protecting group, such as a trialkylsilyl group, for example the trimethylsilyl group. An aryl group includes aryl having 6 to 18 carbon atoms, preferably phenyl, napthyl. An aryl group may be unsubstituted or substituted by groups which are inert under relevant reaction conditions. Hetreocyclyl include heterocyclic groups mentioned below in the meaning of $R_5$ and $R_6$. A heterocyclic group may be unsubstituted or substituted by groups which are inert under relevant reaction conditions.

A compound of formula Ia wherein $R^a$ and $R^d$ denote hydrogen is a tautomeric aldehyde form of a compound of formula I in free base form wherein $R_1$ denotes hydrogen; A compound of formula II may be used as an intermediate in the production of a compound of formula I.

A compound of formula IA, particularly a compound of formula I, Ia or II, is an useful intermediate in the production of highly active antibiotics. It may be used to prepare a wide variety of cephalosporins which are substituted at the nitrogen atom in position 7 and in position 3 of the cephalosprin structure with a wide variety of groups which are useful groups in respect to the activity of the corresponding cephalosporin. A compound of formula I is as such, or, in equilibrium with its tautomeric aldehyde form of formula Ia wherein R denotes a silyl group, suitable as starting material, for example for Wittig reactions, for decarbonylation reactions, for the production of most varied aldehyde derivatives. At the same time one is free to form desired derivatives in position 7, for example by acylation.

Examples of highly active antibiotics which may be obtained from the compounds of the invention in conventional manner are ceftibuten as an example for a decarbonylation product; cefixim, cefdinir, E-1077 or, the compounds of EP 620 225, for example the compounds A to P of EP 620 225, as examples for Wittig products; or compounds having the structure of formula A, disclosed in EP 392 796, as a thioacetal (the thioacetal structure of formula A may be prepared for example according to J. Antibiotics 44(4), 415–21(1991):

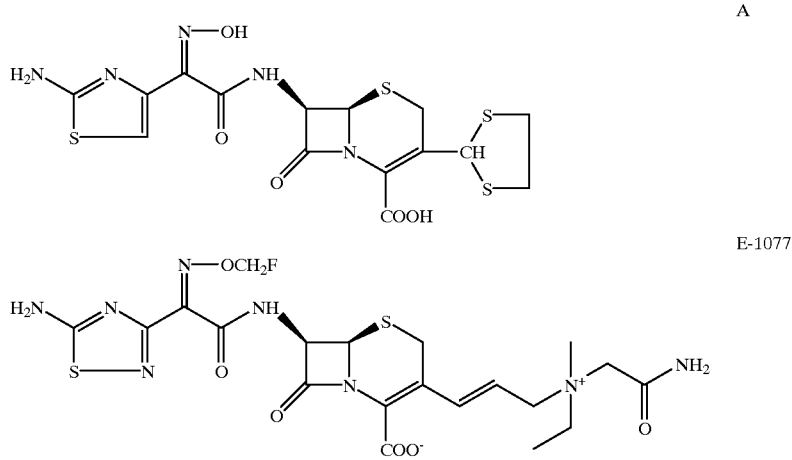

A

E-1077

Processes for the production of a 3-formyl-cephalosporin or of a compound of formula I, which are acylated at the nitrogen atom in position 7 are known from literature. They start exclusively from 7-acylamino-3-hydroxymethyl-3-cephem-4-carboxylic acids (esters), 7-benzylidene-3-hydroxymethyl-3-cephem-4-carboxylic acids (esters), 7-acylamino-3-halogenmethyl-3-cephem-4-carboxylic acid esters or from 7-acylamino-3-cephalosporin lactones.

For example, according to Helvetica Chimica Acta, vol. 57, no. 219, pages 2044ff (1974) by H. Peter and H. Bickel, a 3-formyl-cephalosporin which is acylated at the nitrogen atom in position 7 is produced by means of oxidation of the corresponding 7-phenyl-acetamido-3-hydroxymethyl-3-cephem-4-carboxylic acid benzhydrylester, and subsequently analogues of formula I ($R_1$=H or methyl) which are, however, acylated at the nitrogen atom in position 7 by a phenylacetyl group are produced by cleavage with trifluoro acetic acid in the presence of ortho formic acid methyl ester. Apart from the use of complicated protecting group technology, the process has the particular disadvantage that the oxidation of the alcohol to the aldehyde is accompanied with undesired Δ-2 isomerisation and lactonisation. In addition, the oxidation agents used, such as chromium(VI) oxide, and cleavage reagents, such as trifluoro acetic acid, may not be used in technical scale for ecological reasons.

A process for the production of 7-phenylacetylamino-3-formyl-3-cephem-4-carboxylic acid-p-methoxybenzylester, starting from the corresponding 3-iodomethyl compound, is described by H. Tanaka et al in Synlett, page 660, November 1990. The oxidation agent used is $O_2$ with rhodium chloride and aluminium as catalyst. The oxidation product must be purified by chromatography and the yields are a maximum of 66%.

In DE 2 360 620, a 7-acylamino-3-hydroxymethyl-3-cephem-4-carboxylate is oxidized using chromic acid/sulphuric acid to give the corresponding lactone. Reference is made to stability problems with the corresponding tautomer aldehyde in respect to the lactone form of formula I. The use of chromic compounds is excluded from technical scale for ecological reasons.

Chem. Pharm. Bull. Vol. 28, pages 1339 ff, 1980, describes a process for the production of 7-acylamino-3-formyl-3-cephem-4-carboxylic acid hydroxylactols, starting from the corresponding lactones, via bromination, followed by halogen-hydroxy exchange. The conditions to avoid bromination of the thiazine nucleus must be carefully chosen.

According to the present invention a compound of formula IA, particularly of formulae I, Ia, Ib and II may surprisingly be produced without complicated protecting group technology and without the disadvantages of the prior art specified above. This may take place in a very simple way and results in high yields.

Accordingly, in another aspect the invention relates therefore to a process for the production of a compound of formula IA as defined above by a) for the production of a compound of formula IA, group α), splitting the double bond in position 3 of the ring structure of a compound of formula

III

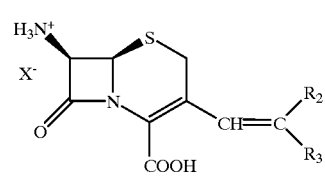

wherein $R_2$ and $R_3$ are the same or different and independently of each other denote hydrogen or an organic group, and $X^-$ is as defined in formula I, in the presence of ozone, and, if desired, converting a compound of formula IA, group α) wherein $R^e$ denotes alkyl, thus obtained, into the corresponding free base of formula Ib

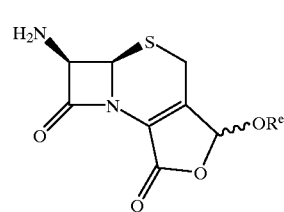

wherein $R^e$ denotes alkyl and, if desired, converting the free base of formula Ib into a salt of formula IA which has a different salt anion than that used in the starting compound of formula III, or b) for the production of a compound of formula IA, group β), treating a compound of formula

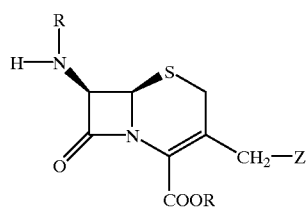

IV wherein R denotes a silyl group, Z denotes $P^+(R_4)_3I^-$ or $P(O)(OR_4)_2$ and $R_4$ denotes lower alkyl or aryl, with at least one strong organic base in combination with a silylation agent and reacting with a nitroso compound of formula

Y—N=O    V wherein Y is as defined in formula IA, and, if desired, converting the free form of formula IA thus obtained in a salt form of formula IA, or c) for the production of a compound of formula IA, group α) which is a compound of formula

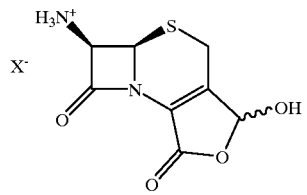

Ic wherein $X^{31}$ is as defined above, treating a compound of formula

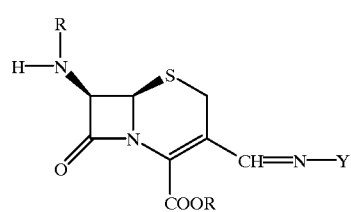

II wherein R denotes a silyl group or a desilylated form thereof of formula

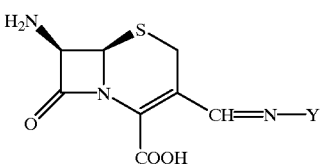

IIa wherein Y is as defined above, with at least one strong aqueous inorganic acid or at least one strong organic acid, or d) for the production of a compound of formula IA, group γ), γα) treating a compound of formula

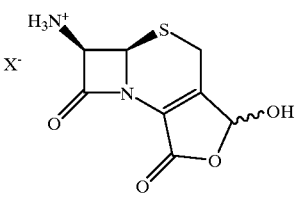

Ic with a base, resulting in a compound of formula

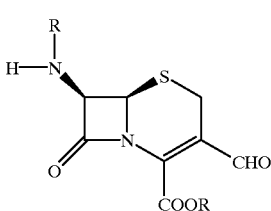

Ia wherein R denotes hydrogen, and, if desired, reacting a compound of formula Ia wherein R denotes hydrogen, with a silylation agent, resulting in a compound of formula Ia wherein R denotes a silyl group, or γα) reacting a compound of formula Ic with a silylation agent, resulting in a compound of formula Ia wherein R denotes a silyl group, and, if desired, converting a compound obtained according to a) to d) in the free form in a salt form thereof or vice versa.

Process a) follows the following reaction scheme:

Compound of formula III

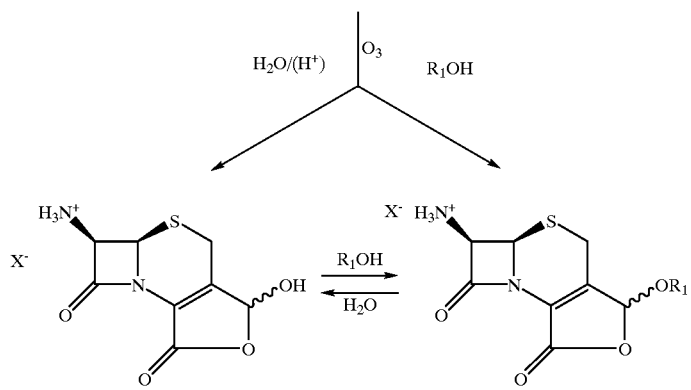

Process a) is an ozonolysis reaction. It may be carried out in a solvent or solvent mixture which contains alcohol or which is alcohol-free with or without the presence of water. Solvents which may be employed include alcohols, such as a straight chain or branched $(C_{1-4})$alcohol; or organic solvents which are inert under the reaction conditions, such as halogenated hydrocarbons, for example dichloromethan; or esters, for example acetic acid esters, in combination with a $(C_{1-4})$alcohol; with or without the presence of water. For example, a compound of formula III (which may be prepared, for example, according to EP 503 453) in which preferably $R_2$ or $R_3$ denotes hydrogen and the corresponding $R_3$ or $R_2$ denotes preferably hydrogen, alkyl, cycloalkyl, aryl, or, a group of formula

—$CH_2$—A wherein A denotes preferably hydrogen, hydroxy, alkoxy, acyloxy, halogen and $X^-$ as defined above, or, the free base of a compound of formula III, treated in an alcohol or in an alcohol-containing solvent mixture with an inorganic or organic acid, is suspended or dissolved in an alcohol or in a solvent mixture containing an alcohol and a solvent which is stable in the presence of ozone, and ozonolysis is carried out in conventional manner. If desired, a reducing agent, such as a sulphide or phosphine may be added to the reaction mixture during or after ozonolysis. The compound of formula IA, group α), wherein $R^a$=H (=compound of formula I wherein $R_1$ is as defined above), may be isolated, for example, by precipitating with an anti-solvent, if desired after (partial) removal of the solvent(mixture). If ozonolysis is carried out in an alcohol-free medium, a compound of formula I wherein $R_1$ denotes hydrogen may be obtained. If ozonolysis is carried out in an alcohol-containing medium, a compound of formula I wherein $R_1$ denotes hydrogen or a compound of formula I wherein $R_1$ denotes alkyl may be obtained. Ozonolysis in an alcohol as solvent and work up at low temperatures may result in a compound of formula I wherein $R_1$ denotes hydrogen. If the reaction mixture is left at elevated temperatures, for example at room temperature, particularly in the presence of an excess of an acid HX wherein X denotes the anion of an inorganic or organic acid, a compound of formula I wherein $R_1$ denotes alkyl may be obtained. If in the alcohol-containing solvent additionally water is present or water is added without an addition of an excess of an acid HX, a compound of formula I wherein $R_1$ denotes hydrogen may be isolated. A compound of formula I wherein $R_1$ denotes hydrogen may be converted into a compound of formula I wherein $R_1$ denotes alkyl by addition of little water or by prolonged standing in an alcohol-containing medium. Conversion of a compound of formula I wherein $R_1$ denotes alkyl into a compound of formula I wherein $R_1$ denotes hydrogen and vice versa may be effected in separate steps as described below.

An isolated compound of formula I wherein $R_1$ denotes alkyl may be easily converted into a compound of formula I wherein $R_1$ denotes hydrogen as follows: A compound of formula I wherein $R_1$ denotes alkyl is dissolved or suspended in water or in an organic solvent mixed with a little water. Acid may be added additionally, and the compound of formula I wherein $R_1$ denotes hydrogen and the corresponding alcohol are formed. The product may precipitate, or, isolation may be effected as conventional, for example by addition of an anti-solvent, optionally after removing the solvent and water. Suitable solvents include water in combination with at least one alcohol, nitriles, e.g. acetonitrile, or ketones, for example acetone. Anti-solvents include solvents for completing precipitation or enhancement of yields, such as organic solvents which are water-free, for example hydrocarbons, ketones, nitriles, ethers or esters.

Alternatively, the compound of formula I wherein $R_1$ denotes hydrogen may be dissolved or suspended in an alcohol or in a solvent mixture containing an alcohol, optionally adding additional acid, and the product of formula I wherein $R_1$ denotes alkyl may be isolated either by simple filtration or it may be precipitated by adding an anti-solvent, optionally after concentration. Suitable solvents include, for example, the corresponding alcohols; nitriles such as acetonitrile; esters such as ethyl acetate; ketones, such as acetone in the presence of the corresponding alcohol; particularly alcohols. Anti-solvents are for example ethers or hydrocarbons. For completing precipitation the reaction mixture may be diluted with hydrocarbons, ketones, nitriles, ethers or esters. Suitable acids include for example (strong) inorganic acids such as hydrohalic acids, nitric acid or perchloric acid and (strong) organic acids, including for example organic sulphonic acids such as benzenesulphonic acid or toluenesulphonic acid.

Surprisingly, no isomeric sulphoxides are produced in the ozonolysis reaction, and similarly, the isolated compounds of formula I are free of undesired Δ-2 compounds. Furthermore polymerisation of a compound of formula I, which may be regarded as aminoaldehyde derivative, is avoided.

In a compound of formula IA a new assymmetric centre is established in the lactol ring due to its production according to the invention. Depending on the reaction conditions mixtures of both diastereoisomers or one or the other of the diastereoisomers may be obtained. The specific diastereoisomer form may be detected, for example, by $^1$H-NMR. The invention relates to both diastereoisomers as well as to mixtures thereof including racemic mixtures. Separation of the diastereoisomers may be carried out in conventional manner, if desired, for example by chromatography.

A compound of formula I wherein $R_1$ denotes alkyl may be converted into a compound of formula Ib wherein $R^e$ denotes alkyl by use of a base and thereafter reconverted in a compound of formula I, wherein $X^-$ is different from the original $X^-$ of the compound of formula III by use of an acid HX wherein X denotes a desired anion of an inorganic or organic acid. Suitable bases include organic amines, such as arylic amines, for example pyridine, or aliphatic amines, for example triethylamine. Suitable solvents for the production of a compound of formula Ib include the corresponding alcohols optionally in combination with an ester, ketone, ether or nitrile.

Process b) relates to the reaction of a compound of formula IV wherein R denotes a silyl group (which may be obtained, for example, by the process described according to EP 503 453), with a nitroso compound of formula V to give a compound of formula IA, group β) (=compound of formula II) in the form of a free base. The reaction may be carried out in the presence of at least one strong organic base in combination with a silylation agent and a solvent. A strong organic base includes, for example, a guanidine or an amidine, such as 1,8-diazybicyclo[5.4.0]-undecene-7-ene (=DBU) or 1,5-diazybicyclo[4.3.0]non-5-en (=DBN); an alkali salt of a nitrogen containing compound, such as the Li or Na salt of hexamethyldisilazane or of an iminophosphorane; a Li salt of a carboxylic acid, such as Li acetate; or an epoxide, such as propylene-oxide or butylene-oxide; preferably propylene-oxide or butylene-oxide. Examples for a silylation agent include bistrimethyl-silylacetamide, bistrimethylsilyl urea. The reaction is preferably carried out in a solvent which is inert under the reaction conditions. Suitable solvents include halogenated hydrocarbons, such as methylene chloride; amides, such as dimethylformamide, dimethylacetamide; ethers, such as tetrahydrofurane. In the case that an epoxide is used, it may act as a base.

About 1 to 1.5 mol, preferably about 1.2 mol of the organic base and about 0.5 to 2 mol, preferably about 1.5 mol of the silylation agent may be used per mol of the starting compound of formula IV.

The chemical nature of the nitroso compound is not critical. A suitable nitroso compound includes an aliphatic, aromatic or heterocyclic nitroso compound, preferably an aromatic nitroso compound, more preferably a nitrobenzene compound, such as p-nitrobenzene. The nitroso comopound may be unsubstituted or in any position substituted, for example by halogen, nitro, alkyl, alkoxy, a nitrogen containing substituent or a functional group, such as carbalkoxy or carboxamido. Equivalent amounts of the starting compound of formula IV and of the nitroso compound of formula V may be used. An excess of one or the other may be useful. The process may be carried out within a broad temperature range, for example at a temperature of between +5 and −20° C.

The silyl groups $R^a$ and $R^d$ in a compound of formula IA, group β), thus obtained may be removed by simple hydrolysis or alcoholysis, for example by addition of an alcohol, for example an $(C_{1-4})$alcohol to the reaction mixture after the reaction between a compound of formula IV and formula V. The desilylated imino compound of formula IIa may precipitate.

A compound of formula IA obtained in free form may be converted into a compound of formula IA in salt form and vice versa in conventional manner.

Process c) is a hydrolysis reaction and results in a compound of formula IA, group α), wherein $R^a$ denotes hydrogen in salt form, i.e. a compound of formula Ic. Hydrolysis is carried out by treating a compound of formula II or of formula IIa with at least one strong inorganic acid, such as hydrochloric acid, hydrobromic acid, sulphuric acid, or at least one strong organic acid, such as a sulphonic acid, for example p-toluene sulfonic acid or methan sulfonic acid in an aqueous solvent or solvent mixture. Solvents for hydrolysis reactions are known. The process may be carried out either after isolation of a compound of formula II, respectively IIa, or directly in the reaction mixture wherein a compound of formula II was prepared. A compound of formula Ic may be separated from the amine which is produced in the course of the reaction, for example by extraction of the aqueous reaction mixture with a water-immiscible solvent or by precipitation of the compound of formula Ic, for example by use of an anti-solvent which is water miscible, such as acetone, acetonitrile or isopropanol, if desired, after concentration by removing of at least a part of the solvent. Isolation of a compound of formula Ic may be carried out for example by lyophilisation.

The reaction of a compound of formula IV into a compound of formula Ic by means of an intermediate of formula II is new and surprising. It is possible to produce a compound of formula I by the process according to the invention in spite of the great tendency towards ring opening of the β-lactam system under hydrolytic conditions (Y. Fujisawa and T. Kanzaki, J. Antibiotics 28, 376, 377; J. E. Baldwin, R. M. Adlington, N. P. Crouch and I. A. C. Pereira, Tetrahedron vol. 49, no. 22, 4915(1993); J. E. Baldwin, K. C. Goh and C. J. Schofield, J. Antibiotics vol. 45, No. 8, 1378–1380, (1992) and the very strong tendency of aminoaldehydes to polymerise due to condensation reactions (Houben Weyl, Methoden der Organischen Chemie, 7/1, pages 156 and 403, Beilstein H 14, pages 23, 28, 30; and E II, page 22).

Process d) is directed to the production of the aldehyde of formula IA, group γ) and concerns a process which influences the tautomeric equilibrium between a compound of formula IA, group α) (formula Ic) and a compound of formula IA group γ) (formula Ia). A compound of formula Ic, for example produced according to process a) or process c) may be used in the production of a compound of formula Ia. An isolated compound of formula Ic, or, a compound of formula Ic formed in situ in the process of its preparation may be used. The reaction may be carried out by addition of a base to the reaction mixture, preferably in the presence of a solvent or solvent mixture which is inert under the reaction conditions. Suitable inert solvent include for example alcohols, such as methanol, nitriles, such as acetonitrile, ketones, such as acetone, esters or halogenated solvents, water or a mixture of solvents mentioned above. Suitable bases include aliphatic or aromatic amines, the conjugated acids of which being soluble in the solvent used, for example triethylamine or pyridine. If water is used as solvent or, if water is present in the reaction mixture, an inorganic base, such as a carbonate or a hydrogen carbonate or the salt of a weak organic acid, such as sodium acetate may be used. The base may be used in an approximately equivalent amount or in an excess, preferably in an approximately equivalent amount in respect to a compound of formula Ic used as starting material. The aminoaldehyde carboxylic acid of formula Ia wherein R denotes hydrogen formed during the reaction may be isolated, for example by filtration if it is insoluble in the reaction medium.

A compound of formula Ia wherein R denotes a silyl group may be obtained from a compound of formula Ia wherein R denotes hydrogen or from a compound of formula Ic by silylation with a silylation agent. Silylation agents include for example N,O bis-trialkylsilylacetamides, such as N,O-bis-trimethylsilylacetamide, N,O-bis-trimethylsilylformamide, N,O-bistrimethylsilyl-trifluoracetamide and silylated ureas such as bis-trimethylsilylurea. Suitable solvents include solvents which are inert toward silylation agents, for example halogenated hydrocarbons; nitriles, such as acetonitrile; esters, for example acetic acid ethyl ester, ethers, for example tert.butyl-methylether, tetrahydrofuran; epoxides, such as propylene oxide, butylene oxide. The amount of the silylation agent may be preferably sufficient for approximately quantitative silylation of the carboxylic acid in position 4 as well as of the amine group in position 7. It has been found that thus a self-condensation of the free amine group with the aldehyde function may be avoided. Particularly, for example, two to three mol of silylation agent may be used per mol of the starting material which is to be silylated.

The compound of formula Ia wherein R denotes hydrogen is surprisingly sufficiently stable to be isolated from aqueous solution; if desired, it may be converted into a bissilyl compound of formula I wherein $R_1$ denotes a silyl group by addition of a silylation agent. A compound of formula I wherein $R_1$ denotes a silyl group is stable and may be further reacted in solution, if desired. Compounds of formula I and of formula Ia are thus indicated for use in the production of antibiotics, for example by acylation at the amine group in position 7 or by reaction of the aldehyde group in position 3 with an aldehyde reagent These reactions may be carried out in conventional manner.

Suitable acylation agents include, for example, activated carboxylic acids, such as acid chlorides, mixed anhydrides or active esters. Acylation may be carried out in conventional manner. Isolation of the N-acylated compound may be carried out as conventional, for example by desilylating with a protic solvent, for example an alcohol or water. The acylated compound may precipitate directly, or may be precipitated with an anti-solvent or in the form of the carboxylic acid salt. It may also be isolated in the form of the corresponding carboxylic acid ester, for example as benzhydrylester, by reacting the desilylated product with diphenyldiazomethane.

The aldehyde function of the compound of formula Ia wherein R is as defined above as well as the latent aldehyde function of its tautomeric form of formula I, wherein $R_1$ denotes hydrogen may be reacted with aldehyde reagents. The choice between the various educts, i.e. for example, a compound of formula Ia wherein R denotes hydrogen; or, the compound which is in an tautomeric equilibrium with a compound of formula Ia, i.e. the compound of formula I wherein $R_1$ denotes hydrogen; or, a compound of formula Ia wherein R denotes a silyl group; depends on the reaction type and the reaction conditions used in each case.

If a conventional nitrogen containing aldehyde reagent is used, such as an amine, hydroxylamine, hydrazine, guanidine or semi-carbazide, all of the educts of formula Ia wherein R is as defined above; or, of formula I wherein $R_1$ denotes hydrogen; may be used.

If a compound of formula Ia is used wherein $R_1$ denotes a silyl group, both groups, i.e. the amine group in position 7 as well as the carboxylic acid group in position 4 of the ring system should be nearly quantitatively silylated because it was found that monosilylation at the carboxylic acid group may result in polymerisation and decomposition.

If the aldehyde-reagent contains groups which may be silylated, the aldehyde-reagent may be conveniently employed as its silylated analogue. The reaction with the corresponding aldehyde reagent is carried out for example in solvents mentioned above for silylation. If desired, the solubility of the aldehyde-reagent may be increased by adding a dipolar, aprotic solvent, such as DMF or sulpholane. The reaction temperature is not critical. The reaction may be carried out, for example, at room temperature or with cooling. Isolation of the reaction product may be effected in conventional manner, for example either by desilylation with a protic solvent, such as an alcohol or water or, by extraction and subsequent isolation from water or an organic solvent (mixture). The product may precipitate.

If it is desired to react the aldehyde function of a compound of formula I wherein $R_1$ denotes hydrogen, it may be reacted in a suitable solvent directly with the desired aldehyde-reagent. If, for example, a nitrogen containing aldehyde-reagent as defined above is used this may be used as free compound or as a salt thereof. Suitable solvents include for example water, polar organic solvents, such as organic amides, ketones, esters, halogenated hydrocarbons, alcohols, organic acids, such as acetic acid. Alcohols may particularly be used in mixture with water. The reaction products may precipitate or may be isolated in conventional manner, for example, by addition of an anti-solvent or by extraction from an organic solvent or solvent mixture.

If it is desired to react the aldehyde function of a compound of formula Ia wherein R denotes hydrogen, an acid may be added to the reaction mixture to enhance solubility of the compound of formula Ia and to increase its reactivity. The reaction may be carried out in tautomeric equilibrium with the compound of formula I wherein $R_1$ denotes hydrogen as described above.

Given the known instability of cephalosporins having an aldehyde group in position 3, the ability of compounds of formula Ia to exist, is new and most surprising.

Some 7-acyl derivates of formula Ia, existing in the form of their isomer hydroxylactones of formula

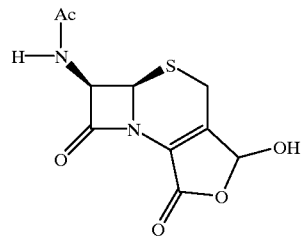

wherein Ac denotes an acyl group, are known.

Trials to convert these hydroxylactones into a salt of the isomer 7-acylamino-3-formyl-4-carboxylic acid of formula

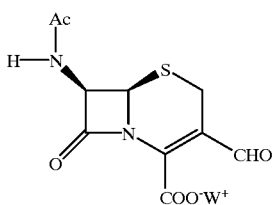

wherein Ac is as defined above and W denotes a cation, may result in decomposition under ring opening of the labile β-lactam ring, particularly in the presence of water.

Existence of a compound of formula Ia is, due to the very strong tendency for aminoaldehydes to polymerise due to self condensation, surprising (see Houben-Weyl; Methoden der Organischen Chemie 7/1, pages 156, 403 and Beilstein H 14, pages 23, 28, 30; E II, page 22).

The compound

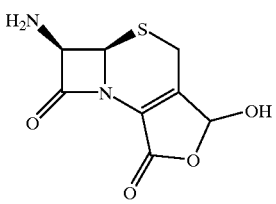

is mentioned in U.S. Pat. No. 3,997,528 as part of a broad class defined by its formula II. No isolation or characterization is described Existence of this compound under the condition given for its production therein is questionable. Morover all previous trials to isolate the compound of formula

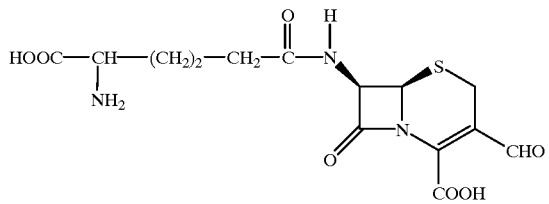

having the free aldehyde in position 3 of the ring system which corresponds to cephalosporin C and which is an envisaged biotransformation product of CefC, failed (see for example Y. Fujisawa and T. Kanzaki, J. Antibiotics 28, pages 376 to 377; J. E. Baldwin, R. M. Adlington, N. P. Crouch and I. A. C. Pereira, Tetrahedron Vol. 49, No. 22, page 4915; J. E. Baldwin, K. C. Goh und C. J. Schofield, J. Antibiotics 45, pages 1378–1380). Instead of the expected structure in all cases the ring open structure of formula

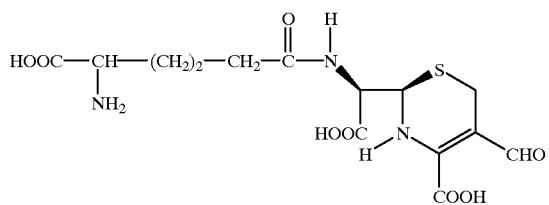

was isolated;

As already mentioned a compound of formula I or of formula Ia may be used as a starting material or as an intermediate in the production of cephalosporins. In a further particular aspect the invention relates therefor to the use of a compound of formula IA in the production of cephalosporins.

In another more particular aspect the invention relates to the use of a compound of formula I as defined in claim 2 wherein $R_1$ denotes hydrogen; or a free form thereof of formula Ib as defined in claim 5 wherein $R^e$ denotes hydrogen; or a compound of formula Ia as defined in claim 3; in the reaction of the free or latent aldehyde function in position 3 of the ring system with a nitrogen containing aldehyde-reagent to give the corresponding product.

In a further particular aspect of the invention a compound of formula I or of formula Ia is suitable in the production of a compound of formula

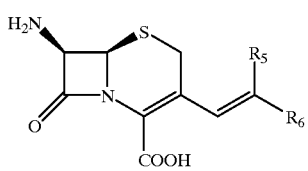

VI wherein $R_5$ and $R_6$ are the same or different and denote hydrogen or an organic group or $R_5$ and $R_6$ denote together a substituted or unsubstituted ring.

An organic group in the meaning of $R_5$ and $R_6$ includes, for example unsubstituted or substituted alkyl, aryl or heterocyclyl. Substitution, for example by halogen, alkoxy, aryloxy, a nitrogen or sulphur containing substituent or a functional group, such as a carbalkoxy or carboxamido group may be in any position. R and & may be part of an unsubstituted or substituted ring system which may contain hetero atoms such as nitrogen, oxygen, sulphur.

For example, one of the substituents $R_5$ or $R_6$ may denote hydrogen and the other a) hydrogen, lower alkyl, lower alkenyl or lower alkinyl;

b) cycloalkyl, cycloalkylalkyl, aryl, arylalkyl, heterocyclyl or heterocyclylalkyl; these groups may be unsubstituted or substituted by lower alkoxy, lower alkylthio, halogen, lower alkyl, nitro, hydroxy, acyloxy, carboxy, carbalkoxy, lower akylcarbonyl, lower alkylsulfonyl, lower alkoxysulfonyl, lower aminoalkylamino, acylamido one or several times, for example one or three times;

c) a group of formula —$CH_2R_7$, wherein $R_7$ denotes

α) hydroxy, lower alkoxy, formyloxy, acetyloxy, lower alkylsulfonyloxy, halogen, N-mono(lower) alkylcarbamoyloxy or N,N-di(lower) alkylcarbamoyloxy, β) heterocyclic group, γ) a group of formula —$S(O)_mR_8$, wherein $R_8$ denotes an aliphatic, araliphatic, alicyclic, aromatic or heterocyclic group and m denotes 0, 1 or 2, or δ) an acyclic or cyclic ammonium group.

"Lower" in this context means $C_{1-6}$, preferably $C_{1-4}$. Suitable heterocyclic groups include for example non-condensed or condensed rings having for example 4 to 7, such as 5 or 6 ring members in each ring. Each ring may, for example, contain up to 4 heteroatoms, such as oxygen, nitrogen or sulphur. The heterocyclic group may be substituted, for example up to three times. Suitable substitutents include for example $(C_{1-4})$alkyl, $(C_{1-4})$alkoxy, halogen, trihalo-$(C_{1-4})$alkyl, hydroxy, oxo, mercapto, amino, carboxyl, carbamoyl, di-$(C_{1-4})$alkylamino, carboxymethyl, carbamoylmethyl, sulfomethyl und methoxycarbonylamino.

Examples for hetercyclic groups include unsubstituted and substituted imidazolyl, diazolyl, triazolyl, tetrazolyl, thiazolyl, thiadiazolyl, thiatriazolyl, oxazolyl, oxydiazolyl, benzimidazolyl, benzoxazolyl, benzothiazolyl, triazolylpyridyl, purinyl, pyridyl, pyrimidinyl, pyridazinyl, pyrazolyl und triazinyl; such as unsubstituted or substituted 4-hydroxy-4-pyridon-2-yl, 1,2,3-triazolyl, 1,2,4-triazolyl, tetrazolyl, oxyzolyl, thiazolyl, 1,3,4-oxydiazolyl, 1,3,4-thiadiazolyl, 1,2,3-thiadiazolyl; particularly 1,5-dihydroxy pyridon-2-yl, 5-hydroxy-1-methyl-4-pyridon-2-yl, 5-hydroxy-4-pyridon-1-yl, 1-methyl-1H-tetrazol-5-yl-2-methyl-1,3,4-thiadiazol-5-yl, 1-carboxymethyl-1H-tetrazol-4-yl, 6-hydroxy-2-methyl-5-oxo-2H-1,2,4-triazin-3-yl, 1,2,3-triazol-5-yl, 4-methylthiazol-5-yl.

Examples of an acyclic amonium group include (1-carbamoyl-2-hydroxyethyl)dime thylamonium, (carbamoylmethyl)(ethyl)-methylamonium, trimethylamonium.

Examples of a cyclic amonium group include pyrrolidinium, which may be mono- or disubstituted at the nitrogen atom by alkyl, carbamoylalkyl, aminoalkyl, carboxyalkyl; pyridinium or cyclopentenopyridinium, which may be substituted at the nitrogen atom by alkyl, halogen, hydroxy, carboxamido, alkoxycarbonyl, amino, monoalkylamino, dialkylamino.

Examples of $R_5$ and $R_6$ as part of an unsubstituted or substituted ring system which may contain hetero atoms such as nitrogen, oxygen, sulphur in each of the rings include for example uncondensed or condensed rings having 3 to 7 ring members, such as 5 or 6 ring members. The rings may be unsubstituted or substituted, for example by $(C_{1-4})$ alkyl, $(C_{1-4})$alkoxy, halogen, trihalo$(C_{1-4})$alkyl, hydroxy, oxo, mercapto, amino, carboxyl, carbamoyl, di$(C_{1-4})$ alkykamino, carboxymethyl, carbamoylmethyl, sulfomethyl methoxycarbonylamino.

Processes for the preparation of compounds of formula VI are known. However, the compounds of formula VI may be prepared according to prior art only by complicated protecting group technology via several reaction steps. For example, particularly two processes via a Wittig or a Horner reaction exist in the preparation of 3-vinylcephalosporins:

The first variant is the reaction of a compound of formula

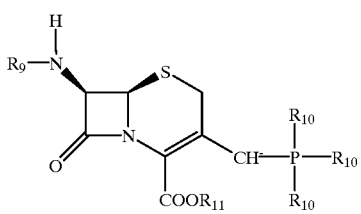

VII or of a compound of formula

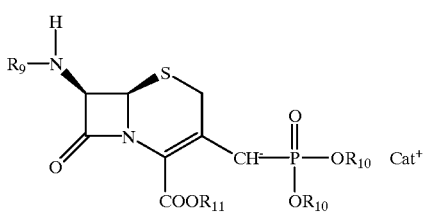

VIII wherein $R_9$ denotes an acyl group or a protecting group, $R_{10}$ denotes aryl, especially phenyl or lower alkyl, $R_{11}$ denotes a cleavable ester protecting group and $Cat^+$ denotes a cation of an alkali metal or the protonated form of a strong organic base, with an aldehyde or ketone of formula

IX wherein $R_5$ and $R_6$ are as defined above, to give the corresponding 3-vinylcephalosporin. After cleavage of $R_9$ and $R_{11}$ a compound of formula VI may be obtained.

Second variant is the reaction of a compound of formula

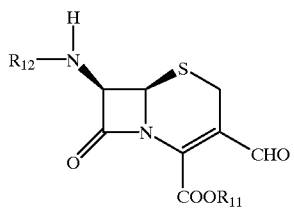

X wherein $R_{12}$ denotes an acyl group or a carbalkoxy group and $R_{11}$ is as defined above with a Wittig reagent of formula

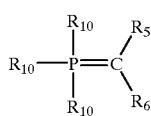

XI or with a Horner reagent of formula

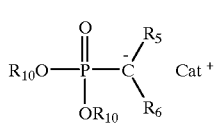

XII wherein $R_5$, $R_6$, $R_{10}$ and $Cat^+$ are as defined above. After cleavage of the protecting groups a compound of formula VI may be obtained.

The second variant, the reaction of a 3-formylcephem compound looks economically favorable in comparison with the first variant in respect to yields, in respect to availability of the corresponding aldehyde or ketone of formula IX (of the first variant), in respect to purities of the products or in respect to the corresponding Z/E content of the product, i.e. the 3-vinyl compounds obtainable by both variants. However, according to prior art the second variant has the following disadvantages: J. A. Webber, J. L. Ott and R. T. Vasileff describe in Journal of Medical Chemistry vol.18, no.10, pages 986ff the reaction of 7-phenyloxyacetamido-3-formyl-3-cephem-4-carboxylic acid tert.butylester-sulfoxide with phosphoranes. A sulphoxide thus obtained has to be reduced and purified by chromatography. Thereafter cleavage of the ester protecting group and cleavage of the phenoxy acetic acid has to be carried out to convert the sulphoxide in the corresponding 7-amino-3-vinyl-3-cephem-4-carboxylic acid. Further purifying steps by chromatography are necessary.

In DOS 2 103 014, experimental part B, example 1(b), the reaction of 7-(2-thienyl)acetamido-3-formyl-3-cephem-4- carboxylic acid diphenylmethylester with ethoxycarbonylt-rimethylene triphenylphosphorane to give the corresponding 3-vinylcephalosporin is described. The impure E-isomer is obtained after purification by chromatography in only 21% yield.

In EP 103 264 is disclosed to convert in a first step 7-[2-(2-formamidothiazol-4-yl)-2-methoximinoacetamido]-3-formyl-3-cephem-4-carboxylic acid benzhydrylester into the corresponding Δ-2-compound which is in a second step reacted in a Wittig reaction to give the corresponding 3-vinyl compound. The 3-vinyl compound has to be purified by chromatography, oxidized to give the corresponding Δ-3-sulphoxide and reduced to give the desired Δ-3-compound.

The process according to the invention avoids the deficiencies of prior art and makes the second variant economically interesting.

In another aspect the invention is therefore directed to a process for the production of a compound of formula

VI

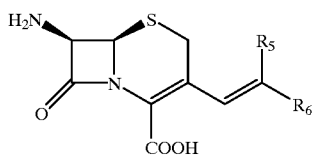

wherein $R_5$ and $R_6$ are the same or different and denote hydrogen or an organic group or $R_5$ and $R_6$ denote together a substituted or unsubstituted ring by reaction of a compound of formula Ia

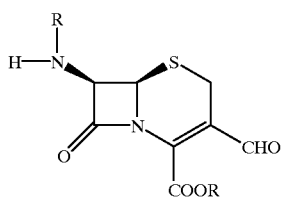

wherein R denotes a silyl group with a compound of formula

XI

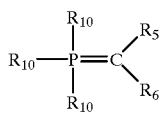

or with a compound of formula

XII

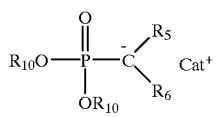

wherein $R_5$ and $R_6$ are as defined above, $R_{10}$ denotes aryl or lower alkyl, and Cat$^+$ denotes a cation of an alkali metal or the protonated form of a strong organic base, to give a compound of formula

XIII

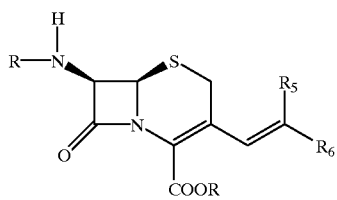

wherein R, $R_5$ and $R_6$ are as defined above and desilylating a compound of formula XIII to give a compound of formula VI.

The Wittig or the Horner reaction may be carried out in a very simple way. For example, N,O-bissilylilated 7-amino-3-formyl-3-cephem-4-carboxylic acid as starting material is reacted with the corresponding phosphoranylidene which is added to the starting material or the reaction is carried out in situ by addition to the starting material of a base of formula

XIV

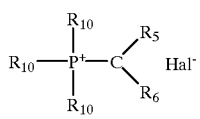

wherein $R_5$, $R_6$ and $R_{10}$ are as defined above and Hal$^-$ denotes an halogen anion, such as chlorine, bromine, iodine, to give the corresponding ylide; or the anion of the corresponding dialkoxy(diaryloxy)phosphinyl compound is added to the starting material. After termination of the reaction the compound of formula VI may be isolated, for example in conventional manner, i.e. by hydrolysis of the silyl groups with a protic solvent such as water or alcohol or, the compound is isolated, for example, by extraction and precipitated around the isoelectric pH.

Suitable solvents for the Wittig or Horner reaction include solvents which are inert toward silylation agents, such as halogenated hydrocarbons, for example methylene chloride; N,N-dialkylamides, for example DMF; nitriles, for example acetonitrile; esters, for example alkyl acetate, such as ethyl acetate; ethers, for example tetrahydrofuran or methyl-tert.butyl-ether; epoxides (which may act at that same taime also as a base), such as propylene oxide or butylene oxide; or mixtures thereof. The reaction temperatures for Wittig or Horner reactions are not critical. The reaction may be carried out, for example, with cooling below or around 0° C. Depending on the ylide used lower or higher temperatures may be used.

Suitable bases for the in situ formation of the ylide from the corresponding phosphonium salt include for example epoxides (which may act at the same time as a solvent), such as propylene oxide; or a salt of a carboxylic acid in combination with a silylation agent. The silylation agent may be used to neutralize the carboxylic acid formed in the course of the reaction as a silyl compound. Suitable silylation agents include for example N,O-bistrimethylsilylacetamide (=BSA), N,O-bistrimethylsilyltrifluoracetamide.

If a phosphonium salt, a phosphoranylene compound or a phosphinyl compound (=phosphoric compound) used contain groups which may be silylated, the phosphoric compound may be silylated before the Wittig or Horner reaction.

The stoichiometry of the aldehyde compound and the phosphoric compound which may be applied depends on the basic strength of the phosphoric compound used. The aldehyde or the phosphoric compound may be used in an excess or both are used in approximately equimolar amounts. If ylides or phosphinyl anions having a high base strength are used the compound of formula Ia should rather be used in an excess than the ylide or the phosphinyl anion.

The compounds of formula Ia or of formula XIII have under the reaction conditions surprisingly low tendency to form Δ-2 compounds. No or almost no Δ-2 compounds may be formed if stabilized ylides are used. Additionally, Δ-2 compounds which might be formed in the course of the reaction are depleted in the course of work up.

The process according to the invention shows high trans selectivity in respect to the double bond formed during the reaction. If, for example, a compound of formula Ia is reacted with ethoxycarbonylmethylene triphenylphosphorane surprisingly only the trans compound is in praxi isolated. This is in contrast to results of S. C. M. Fell et al., J. Chem. Soc. Perkin I, 1361ff, 1991 wherein the reaction of 7-phenylacetamido-3-formyl-3-cephem-4-carboxylic acid benzhydrylester with methoxycarbonylmethylene triphenylphosphorane results in a product containing about 8 to 9% of the cis isomer.

Advantages of this process according to the invention as regards prior art are simple feasibility of the reaction; simple work up; high insensibility of the system in respect to Δ-2 isomerisation; and trans selectivity in the Wittig or Horner reaction.

The following examples define the invention more specific without restricting its scope. All temperatures indicated are in degree Celsius and are uncorrected. Mixtures of isomers obtained according to the examples may be separated, for example by chromatography.

EXAMPLE 1

Hydrochloride of 6-amino-1,4,5a,6-tetrahydro-3-hydroxy-1,7-dioxo-3H,7H-aceto[2,1-b]furo[3,4-d][1,3]thiazine (hydroxylactone of the hydrochloride of 7-amino-3-formyl-3-cephem-4-carboxylic acid) (process a)

13.8 g of 7-amino-3-[Z(/E)-prop-1-en-1-yl]-3-cephem-4-carboxylic acid-hydrochloride (7-PACA) are dissolved in 200 ml of methanol and the slightly yellowish solution is cooled to −50°. At this temperature 8 l of $O_2$ containing ca. 2 percent by volume of ozone per minute are introduced into this solution whilst stirring. Ozonolysis is complete after approximately 20 minutes. HPLC indicates a practically quantitative and uniform reaction of the starting compound into the title compound. 8 l of $N_2$ are passed through the reaction mixture in ca. 2 minutes, and the slightly cloudy solution is poured into 1400 ml of methyl tert.butyl ether whilst stirring. The precipitated product is filtered under $N_2$, washed with a little methyl tert.butyl ether and acetonitrile, and dried in a vacuum drying chamber over a drying agent. The hydrochloride of 6-amino-1,4,5a,6-tetrahydro-3-hydroxy-1,7-dioxo-3H,7H-aceto[2,1-b]furo[3,4-d][1,3]thiazine is obtained in the form of a white powder with a purity (HPLC) of over 95%.

$^1$H-NMR ($D_2O$+DCl): 3.62 ($AB_q$, J=16 Hz, 2H, S—$CH_2$); 5.10 (2d, J=5 Hz, 2H, β-lactam H); 6.20 (s, broad, 1H, O—CH—O).

EXAMPLE 2

Tosylate of 6-amino-1,4,5a,6-tetrahydro-3-hydroxy-1,7-dioxo-3H,7H-aceto[2,1-b]furo[3,4-d][1,3]thiazine (hydroxylactone of the tosylate of 7-amino-3-formyl-3-cephem-4-carboxylic acid) (process a)

12 g of 7-PACA are suspended in 200 ml of methanol, and brought into solution by adding 9.5 g of p-toluenesulphonic acid hydrate. This solution is ozonised and worked up as described in example 1. The tosylate of 6-amino-1,4,5a,6-tetrahydro-3-hydroxy-1,7-dioxo-3H,7H-aceto[2,1-b]furo[3,4-d][1,3]thiazine is obtained as a slightly yellowish powder.

$^1$H-NMR (DMSO-$d_6$): 2.35 (s, 3H, $CH_3$); 3.7–3.9 (m, 2H, S—$CH_2$); 5.1–5.4 (m, 2H, β-lactam H); 6.3 (d, broad, 1H, O—CH—O); 7.1 and 75 ($A_2B_2$, J=7 Hz, 4H, Ar—H).

EXAMPLE 3

Hydrochloride of 6-amino-1,4,5a,6-dihydro-3-methoxy-1,7-dioxo-3H,7H-aceto[2,1-b]furo[3,4-d][1,3]thiazine (methoxylactone of the hydrochloride of 7-amino-3-formyl-3-cephem-4-carboxylic acid) (process a) 13.8 g of 7-PACA hydrochloride are dissolved in 250 ml of methanol, ozonised as described in example 1, and precipitated with methyl tert.butyl ether. The product is filtered off, suspended in 200 ml of acetonitrile whilst in a moist, methanol-containing state, and the suspension is stirred for ca. 30 minutes. The precipitate which is the hydrochloride of 6-amino-1,4,5a,6-dihydro-3-methoxy-1,7-dioxo-3H,7H-aceto[2,1-b]furo[3,4-d][1,3]thiazine is isolated and dried in a vacuum drying chamber over phosphorus pentoxide (yellowish powder).

$^1$H-NMR (DMSO $d_6$): 3.55 (s, 3H, O—$CH_3$); 3.8 ($AB_q$, J=4 Hz, 2H, S—$CH_2$); 5.3 (2d, J=5 Hz, 2H, β-lactam H); 6.2 (s, 1H, O—CH—O).

EXAMPLE 4

Hydrochloride of 6-amino-1,4,5a,6-tetrahydro-3-methoxy-1,7-dioxo-3H,7H-aceto[2,1-b]furo[3,4-d][1,3]thiazine (methoxylactone of the hydrochloride of 7-amino-3-formyl-3-cephem-4-carboxylic acid)(process a)

13.3 g of 7-amino-3-[(Z/E)-3-acetoxy-1-prop-1-en-1-yl]-3-cephem-4-carboxylic acid are suspended in ca. 230 ml of methanol. 13.1 g of triphenylphosphine are added, and a solution is obtained after adding 10 ml of diisopropylether containing ca. 1 g of dry HCl, followed by a further 100 rml of methanol. The solution is ozonised as in example 1, but a total of ca. 2.4 molar equivalents of ozone are introduced over the course of ca. 30 minutes. After removing of an eventual residue of ozone with $N_2$, the reaction mixture is discharged onto ca. 1800 ml of methyl tert.butyl ether. The hydrochloride of 6-amino-1,4,5a,6-tetrahydro-3-methoxy-1,7-dioxo-3H,7H-aceto[2,1-b]furo[3,4-d][1,3]thiazine precipitates.

The $^1$H-NMR spectrum is identical to the spectrum reproduced in example 3.

EXAMPLE 5

Hydrochloride of 6-amino-1,4,5a,6-tetrahydro-3-methoxy-1,7-dioxo-3H,7H-aceto[2,1-b]furo[3,4-d][1,3]thiazine (methoxylactone of the hydrochloride of 7-amino-3-formyl-3-cephem-4-carboxylic acid)

1 g of 6-amino-1,4,5a,6-tetrahydro-3-hydroxy-1,7-dioxo-3H,7H-aceto[2,1-b]furo[3,4 d][1,3]thiazine hydrochloride are dissolved in 5 ml of methanol. Ca 0.5 ml of diisopropyl ether, which has been mixed with HCl gas, are added and the mixture is stirred for ca. 10 minutes. The hydrochloride of 6-amino-1,4,5a,6-tetrahydro-3-methoxy-1,7-dioxo-3H,7H-aceto[2,1-b]furo[3,4-d][1,3]thiazine is precipitated by addition of ca. 50 ml of acetonitrile. Only one of the diastereoisomers in respect to position 3 is obtained.

$^1$H-NMR (300 MHz, DMSO-$d_6$): 3.48(s,3H,O—$CH_3$); 3.73 and 3.89($AB_q$,J=18 Hz,2H,S—$CH_3$); 5.22 and 5.32 ($AB_q$,J=5 Hz, 2H,β-lactam H); 6.17(s,1H,O—CH—O).

EXAMPLE 6

Hydrochloride of 6-amino-1,4,5a,6-tetrahydro-3-ethoxy-1,7-dioxo-3H,7H-aceto[2,1-b]furo[3,4-d][1,3]thiazine (ethoxylactone of the hydrochloride of 7-amino-3-formyl-3-cephem-4-carboxylic acid)

5 g of the hydrochloride of 6-amino-1,4,5a,6-tetrahydro-3-hydroxy-1,7-dioxo-3H,7H-aceto[2,1-b]furo[3,4-d][1,3]thiazine are dissolved in 30 ml ethanol. Ca. 2 ml of diisopropyl ether, which has been mixed with HCl gas, are added and the mixture is stirred for ca. 10 minutes. The solvent is removed in vacuo, the residue is treated with methyl-tert.butylether and filtered off. The precipitate is a mixture of the diastereoisomers of the hydrochloride of 6-amino-1,4,5a,6-tetrahydro-3-ethoxy-1,7-dioxo-3H,7H-aceto[2,1-b]furo[3,4-d][1,3]thiazine in respect to position 3 of ca. 9:11.

$^1$H-NMR (300 MHz, DMSO-$d_6$): 1.18 (2t, J=7 Hz, 3H, $CH_3$); 3.37 (2q, 2H, $CH_2$—$CH_3$); 3.9 (m, 2× ABq, 2H, S—$CH_2$); 5.20 (d), resp. 5.22 (d) and 5.31 (2 isochrone d) (2× ABq, J=5 Hz, 2H, β-lactam H); 6.21 and 6.31 (s, 1H, O—CH—O).

EXAMPLE 7
Hydrochloride of 6-amino-1,4,5a,6-tetrahydro-3-propoxy-1,7-dioxo-3H,7H-aceto[2,1-b]furo[3,4-d][1,3]thiazine (propoxylactone of the hydrochloride of 7-amino-3-formyl-3-cephem-4-carboxylic acid)

5 g of the hydrochloride of 6-amino,1,4,5a,6-tetrahydro-3-hydroxy-1,7-dioxo-3H,7H-aceto[2,1-b]furo[3,4-d][1,3]thiazine are dissolved in 50 ml n-pmpanol. Ca. 2 ml of diisopropyl ether, which has been mixed with HCl gas, are added and the mixture is stirred for ca. 10 minutes. The solvent is removed in vacuo, the residue is treated with methyl-tert.butylether and filtered off. The precipitate is a mixture of the diastereoisomers of the hydrochloride of 6-amino-1,4,5a,6-tetrahydro-3-propoxy-1,7dioxo-3H,7H-aceto[2,1-b]furo[3,4-d][1,3]thiazine in respect to position 3 of ca. 1:1.

$^1$H-NMR (300 MHz, DMSO-$d_6$): 0.85 (2t, J=7 Hz, 3H, $CH_3$); 1.6 (m, 2H, $CH_2$—$CH_3$); 3.7 (m, 2H, O—$CH_2$); 4.9 (m, 2× ABq, 2H, S—$CH_2$); 5.20 (d), resp. 5.21 (d) and 5.31 (2 isochrone d) (ABq, J=5 Hz, 2H, β-lactam H); 6.21 and 6.3 (s, 1H, O—CH—O).

EXAMPLE 8
Tosylate of 6-amino-1,4,5a,6-tetrahydro-3-methoxy-1,7-dioxo-3H,7H-aceto[2,1-b]furo[3,4-d][1,3]thiazine (methoxylactone of the tosylate of 7-amino-3-formyl-3-cephem-4-carboxylic acid)

15 g of the hydrochloride of 6-amino-1,4,5a,6-tetrahydro-3-methoxy-1,7-dioxo-3H,7H-azeto[2,1-b]furo[3,4-d][1,3]thiazine are dissolved in 30 ml methanol. 20 ml of tributylamine are added at 0° and the mixture is stirred for ca. 15 minutes. The precipitate is filtered off and washed with a little methanol (0°). The free base of 6-amino-1,4,5a,6-tetrahydro-3-methoxy-1,7-dioxo-3H,7H-aceto[2,1-b]furo[3,4-d][1,3]thiazine thus obtained is a brown powder containing only one of the diastereomers in respect to position 3.

$^1$H-NMR (300 MHz, $CD_2Cl_2$): 3.51 and 3.61 (ABq, J=18 Hz, 2H, S—$CH_2$); 3.56 (s, 3H, $CH_3$); 4.91 (s, broad) and 4.97 (ABq, J=5 Hz, 2H, β-lactam H); 5.82 (s, 1H, O—CH—O).

1 g of the free base obtained as described above is dissolved in 10 ml of methylenchloride and treated with a solution of 780 mg of p-toluenesulfonic acid monohydrate in 1 ml of methanol. After 5 minutes the solvent is removed in vacuo and the residue is treated with diethylether and filtered. Slightly coloured crystals of one of the diastereoisomers of the tosylate of 6-amino-1,4,5a,6tetrahydro-3-methoxy-1,7-dioxo-3H,7H-aceto[2,1-b]furo [3,4-d][1,3]thiazine are thus obtained.

$^1$H-NMR (300 MHz, DMSO-$d_6$): 3.48 (s, 3H, $CH_3$); 3.75 and 3.88 (ABq, J=18 Hz, 2H, S—$CH_2$); 5.23 and 5.32 (ABq, J=5 Hz, 2H, β-lactam H); 6.2 (s, 1H, O—CH—O); 7.1 and 7.48 ($A_2B_2$, J=8 Hz, 4H, ArH).

EXAMPLE 9
7-Amino-3-(N-phenylimino)methyl-3-cephem-4-carboxylic acid (process b)

106.5 ml of bistrimethylsilyl acetamide and 412 ml of propylene oxide are added at 0° to 212.8 g of 7-trimethylsilylamino-3-triphenylphosphoniummethyl-3-cephem-4-carboxylic acid-trimethylsilyl ester iodide in 460 ml of dry dimethylformamide. The solution is subsequently stirred at this temperature for 3 hours. 119.6 g of p-nitrosobenzene are added. After stirring for 16 hours at −13°, the dark-coloured reaction solution is stirred into 2400 ml of ethanol at this temperature. The product precipitates. After stirring for 30 minutes in a cooling bath, the deposit is filtered off, washed with cold ethanol and dried.

$^1$H-NMR ($CDCl_3$+BSA): 0.09 (s, 9H, N—Si($CH_3$)$_3$); 0.25 (s, 9H, O—Si($CH_3$)$_3$); 1.87 (d, J=9.4 Hz, 1H, NH—Si($CH_3$)$_3$); 4.04 ($AB_q$, J=18.5 Hz, 2H, S—$CH_2$); 4.87 (2d, J=9.4 Hz, J=5.3 Hz, 11H, β-lactam-H); 5.06 (d, J=5.3 Hz, 1H, β-lactam-H); 7.14–7.41 (m, 5H, aromatics-H); 8.72 (s, 1H, CH=N).

EXAMPLE 10
Hydrochloride of 6-amino-1,4,5a,6-tetrahydro-3-hydroxy-1,7-dioxo-3H,7H-aceto[2,1-b]furo[3,4-d][1,3]thiazine (hydroxylactone of the hydrochloride of 7-amino-3-formyl-3-cephem-4-carboxylic acid) (process c)

5 g of 7-amino-3-(N-phenylimino)methyl-3-cephem-4-carboxylic acid are introduced into 150 ml of 2 N hydrochloric acid at 0°. After stirring for 10 minutes at this temperature, the small amount of insoluble starting material is separated by filtration. The clear filtrate is washed several times with isobutanol in order to remove aniline, and is lyophilised. The hydrochloride of 6-amino-1,4,5a,6-tetrahydro-3-hydroxy-1,7-dioxo-3H,7H-aceto[2,1-b]furo[3,4-d][1,3]thiazine is thus obtained as a light bright-yellow powder.

$^1$H-NMR ($D_2O$+DCl): 3.77 ($AB_q$, J=18 Hz, 2H, S—$CH_2$); 5.22 (d, J=5.2 Hz, 1H, β-lactam H); 5.27 (d, J=5.2 Hz, 1H, β-lactam H); 6.35 (s, broad, 1H, O—CH—O).

EXAMPLE 11
Hydrochloride of 6-amino-1,4,5a,6-tetrahydro-3-hydroxy-1,7-dioxo-3H,7H-aceto[2,1-b]furo[3,4-d][1,3]thiazine (hydroxylactone of the hydrochloride of 7-amino-3-formyl-3-cephem-4-carboxylic acid) (processes b+c)

13.4 ml of bistrimethylsilyl acetamide and 51.5 ml of propylene oxide are added at 0° to 26.6 g of 7-trimethylsilylamino-3-triphenylphosphoniummethyl-3-cephem-4-carboxylic acid-trimethylsilyl ester iodide in 50 ml of hexamethyldisilanane-containing dichloromethane. The solution is stirred at this temperature for one hour. 7.9 g of p-nitrosobenzene are added. After stirring for 18 hours at 0°, the propylene oxide is distilled off in vacuo. The reaction mixture is stirred into 100 ml of cold 1 N hydrochloric acid. After separation of the phases the aqueous phase is washed several times with isobutanol to separate aniline and lyophilised. The hydrochloride of 6-amino-1,4,5a,6-tetrahydro-3-hydroxy-1,7-dioxo-3H,7H-aceto[2,1-b]furo[3,4-d][1,3]thiazine is thus obtained as a light yellowish coloured powder.

Work up the reaction mixture may also be carried out as follows: The residue after evaporation is stirred into 100 ml of cold 1 N hydrochloric acid and stirred for 10 minutes at 0°. The 2-phase mixture is filtered blank. After phase separation the product-containing aqueous phase is washed several times with isobutanol. The aqueous phase is concentrated in vacuo and purified over an absorber resin HP20. The fractions containing the product are combined and lyophilised. The hydrochloride of 6-amino-1,4,5a,6-tetrahydro-3-hydroxy-1,7-dioxo-3H,7H-aceto[2,1-b]furo[3,4-d][1,3]thiazine is thus obtained as a white powder.

The $^1$H-NMR spectrum is identical to the spectrum of example 1.

EXAMPLE 12
(6R-trans)-7-amino-3-formyl-8-oxo-5-thia-1-azabicyclo[4.2.0]oct-2-ene-2-carboxylic acid (=7-amino-3-formyl-3-cephem-4-carboxylic acid)(process d)

2.64 g of the hydrochloride of 6-amino-1,4,5a,6-tetrahydro-3-hydroxy-1,7-dioxo-3H,7H-aceto[2,1-b]furo[3,4-d][1,3]thiazine (hydroxylactone of the hydrochloride of 7-amino-3-formyl-3-cephem-4-carboxylic acid) are dissolved in 50 ml of methanol. A solution of 0.78 g of pyridine in 10 ml of methanol is added dropwise to this solution whilst stirring and cooling with ice. The precipitated product is filtered off under nitrogen whilst excluding moisture, washed with a little methanol and dried over a drying agent in vacuo at room temperature. (6R-trans)-7-amino-3-formyl-8-oxo-5-thia-1-azabicyclo[4.2.0]oct-2-ene-2-carboxylic acid is thus obtained in the form of a light brown powder. IR (KBr): 1799 cm$^{-1}$ (β-lactam), 1672 cm$^{-1}$ (CHO), 1606 and 1542 cm$^{-1}$ (carboxylate) UV spectrum: $\lambda_{max}$ in H$_2$O=302 nm.

EXAMPLE 13
7-trimethylsilylanmino-3-formyl-3-cephem-4-carboxylic acid trimethylsilylester (process d)

A suspension of 100 mg of 6-amino-1,4,5a,6-tetrahydro-3-hydroxy-1,7-dioxo-3H,7H-aceto[2,1-b]furo[3,4-d][1,3]thiazine (hydroxylactone of the hydrochloride of 7-amino-3-formyl-3-cephem-4-carboxylic acid) in 1 ml of deuterochloroform is mixed at room temperature with 0.28 ml of BSA. The reaction mixture is stirred for 10 minutes at room temperature. A clear solution is obtained. The reaction solution has the following $^1$H-NMR spectrum:

1.40 (d, J=12 Hz, 1H, NH-[TMS]$_2$); 3.57 (AB$_q$, J=18.3 Hz, 2H, S—CH$_2$); 4.80 (2d, J=12 Hz, J=5.3 Hz, 1H, β-lactam-H); 4.90 (d, J=5.3 Hz, 1H, β-lactam-H); 9.81 (s, 1H, CH=O). 7-trimethylsilylamino-3-formyl-3-cephem-4-carboxylic acid trimethylsilylester may be obtained from this solution by means of evaporation.

EXAMPLE 14
7-trimethylsilylamino-3-formyl-3-cephem-4-carboxylic acid trimethylsilylester 2.28 g of 7-amino-3-formyl-3-cephem-4-carboxylic acid are stirred for 15 minutes at 0° in a mixture of 50 ml of dichloromethane and 20 ml of acetonitrile with 5.4 ml of N,O-bis-(trimethylsilyl)acetamide. A light yellow solution is obtained. 7-trimethylsilylamino-3-formyl-3-cephem-4-carboxylic acid trimethylsilylester may be obtained from this solution by means of evaporation.

EXAMPLE 15
(6R-trans)-7-amino-3-formyl-8-oxo-5-thia-1-azabicyclo[4.2.0]oct-2-en-2-carboxylic acid (7-amino-3-formyl-3-cephem-4-carboxylic acid) (processes a+d)

A solution of 956 g 7-amino-3-[(E/Z)-prop-1-en-1-yl]-3-ephem-4-carboxylic acid-hydrochloride in 7 l methanol is ozonized as described in example l(temperature: −50°; 10 oxygen containing ca. 4 percent by volume of ozoneiminute are introduced). Ozonolysis is terminated after ca. 4 hours. 40 l of N$_2$ are passed through the reaction mixture in ca. 5 minutes. The reaction temperature is raised to −35° and 5.6 l of an aqueous, 5% wäßrigen solution of sodium acetate are added whilst stirring without further cooling. The precipitate is immediately filtered under nitrogen whilst excluding of moisture, washed 2 times with 2.5 l of acetonitrile and dried in a drying chamber at 30° for 5 hours. (6R-trans)-7-amino-3-formyl-8-oxo-5-thia-1-azabicyclo[4.2.0]oct-2en-2-carboxylic acid is thus obtained as a light yellowish powder.

IR(KBr): 1799 cm$^{-1}$ (β-lactam), 1672 cm$^{-1}$ (CHO), 1606 and 1542 cm$^{-1}$ (carboxylate) UV-spectrum: $\lambda_{max}$ in H$_2$O= 302 nm.

Compounds of formulae I, Ia and II may be used for the production of cephalosporins, for example for the production of

16) N-(1,4,5a,6-tetrahydro-3-methoxy-1,7-dioxo-3H,7H-aceto[2,1-b]furo[3,4-d][1,3]thiazin-6-yl)-phenylacetic acid amide 2 g of the tosylate of 6-amino1,4,5a,6-tetrahydro-3-methoxy-1,7-dioxo-3H,7H-aceto[2,1-b]furo[3,4-d][1,3] thiazine are dissolved in 50 ml methylenchloride, cooled to 0° and treated with 1.85 g of N,O-bis(trimethylsilyl)-acetamide. After 30 minutes 1.4 g of phenylacetic acid chloride are added and the reaction mixture is stirred for about 30 minutes at room temperature. 2 ml of methanol are added followed by 5 minutes of stirring at room temperature and filtration. After removal of the solvent the residue is treated with 50 ml of methyl-tert.butylether and with 20 ml of methanol and filtered. One of the diastereomers of N-(1,4,5a,6-tetrahydro-3-methoxy-1,7dioxo-3H,7H-aceto[2,1-b]furo[3,4-d][1,3]thiazin-6-yl)-phenylacetic acid amide is thus obtained in the form of a colourless powder.

$^1$H-NMR (300 MHz, CD$_2$Cl$_2$): 3.50 and 3.60 (ABq, J=18 Hz, 2H, S—CH$_2$); 3.57 (s, 3H, CH$_3$); 3.63 (AB, 2H, CH$_2$); 5.0 (d, J=5 Hz, 1H, β-lactam H); 5.80 (s, 1H, O—CH—O); 5.94 (dd, J=9 Hz and 5 Hz, 1H, β-lactam H); 6.4 (d broad, J=9 Hz, NH); 7.23–7.4 (m, 5H, Ar—H).

$^1$H-NMR (300 MHz, DMSO-d$_6$): 3.40 (s, 3H, CH$_3$); 3.49 und 3.55 (ABq, J=13 Hz, 2H, CH$_2$); 3.61 and 3.76 (ABq, J=18 Hz, 2H, S—CH$_2$); 5.11 (d, J=5 Hz, 1H, β-lactam H); 5.87 (dd, J=8 Hz und 5 Hz, 1H, β-lactam H); 6.12 (s, 1H, O—CH—O); 7.2–7.3 (m, 5H, Ar—H); 9.20 (d, J=8 Hz, 1H, NH).

17) 7-amino-3-(N-phenylimino)methyl-3-cephem-4-carboxylic acid

A suspension of 0.50 g of the hydrochloride of 6-amino-1,4,5a,6-tetrahydro-3-hydroxy-1,7-dioxo-3H,7H-aceto[2,1-b]furo[3,4-d][1,3]thiazine in 5 ml of chloroform is mixed at 0° with 2.3 ml of BSA and stirred for 15 minutes. A clear solution is obtained. 0.35 ml of aniline are added. After stirring for 3 hours at 0°, the reaction mnixture is stirred into 30 ml of cold ethanol. The imino compound precipitates. After stirring for 30 minutes in the cooling bath, the deposit is filtered off, washed with ethanol and dried.

$^1$H-NMR (CDCl$_3$+BSA): 1.87 (d, J=9.4 Hz, 1H, NH-(TMS)$_2$); 4.04 (AB$_q$, J=18.5 Hz, 2H, S—CH$_2$); 4.87 (2d, J=9.4 Hz, J=5.3 Hz, 1H, β-lactam-H); 7.14–7.41 (m, 5H, aromatic H); 8.72 (s, 1H, CH=N). IR(KBr): 1789 cm$^1$ (C=O, β-lactam).

18) [5aR(5aα,6β)]-1,4,5a,6-tetrahydro-3-hydroxy-6-phenylacetamido-3H,7H-aceto[2,1-b]furo[3,4-d][1,3]thiazine-1,7(4H)-dione(=hydroxylactone of 7-phenylacetamido-3-formyl-3-cephem-4-carboxylic acid)

2.85 ml of N,O-bis-(trimethylsily)-acetamide are added at 0° to a suspension of 1.39 g of 6-amino 1,4,5a,6-tetrahydro- 3-hydroxy-1,7dioxo-3H,7H-aceto[2,1-b]furo[3,4-d][1,3] thiazine in a mixture of 50 ml of dichloromethane and 10 ml of acetonitrile. After stirring for 10 minutes, a clear solution is obtained, into which 0.6 ml of phenylacetic acid chloride are added dropwise. The reaction mixture is stirred for 30 minutes at 0° and 0.2 ml of water are added. After separating the precipitated acetamide-HCl, evaporation is effected in vacuo. The residue is treated with methyl-tert.butyl ether and dried. [5aR(5aα,6β)]-1,4,5a,6-tetrahydro-3-hydroxy-6-phenylacetamido-3H,7H-aceto[2,1-b]furo[3,4-d][1,3]thiazine-1,7(4H)-dione is thus obtained in the form of a light yellow powder.

$^1$H-NMR (60 MHz, d$_6$-DMSO): 3.5 (s, 2H, —CH$_2$—CO); 3.75 (s, broad, 2H, SCH$_2$); 5.1 (d, J=5 Hz, 1H); 5.9 (dd, J=5 and 8 Hz, 1H); 6.25 (d, J=6 Hz, 1H, O—CH—O); 7.25–7.3 (s, broad, 5H, Ar—H); 9.2 (d, J=7 Hz, 1H, NH).

19) Sodium salt of 7-phenylacetamido-3-formyl-3-cephem-4-carboxylic acid 2.28 g of 7-amino-3-formyl-3-cephem-4-carboxylic acid are stirred for 15 minutes at 0° in a mixture of 50 ml of dichloromethane and 20 ml of acetonitrile with 5.4 ml of N,O-bis-(trimethylsilyl)-acetamide. 1.32 ml of phenylacetic acid chloride are added dropwise to the light yellow solution obtained. The reaction mixture is stirred for 30 minutes at 0°, and is then hydrolysed with 0.4 ml of water. The cloudy brown solution is filtered until clear, and the dichloromethane removed in vacuo. The residue is diluted with 20 ml of acetonitrile and then mixed whilst stirring with 1.7 g of sodium-2-ethylhexanoate. Stirring continues for 10 minutes at room temperature, and the precipitated product is filtered. After drying in a vacuum, the sodium salt of 7-phenylacetamido-3-formyl-3-cephem-4-carboxylic acid is thus obtained.

$^1$H-NMR (60 MHz, d$_6$-DMSO): 3.45 (AB$_q$, J=15 Hz, 2H, SCH$_2$); 3.60 (s, 2H, —CH$_2$—CO); 5.1 (d, J=5 Hz, 1H); 5.65 (dd, J=5 and 8 Hz, 1H); 7.2–7.5 (s, broad, 5H, Ar—H); 9.2 (d, J=7 Hz, 1H, NH); 9.7 (s, 1H, CH=O).

20) 7-phenylacetamido-3-formyl-3-cephem-4-carboxylic acid benzhydrylester 2.28 g of 7-amino3-formyl-3-cephem-4-carboxylic acid are bisilylated as described in example 19 with 5.4 ml of N,O-bis-(trimethylsilyl)acetamide, reacted with phenylacetic acid chloride, and then hydrolysed with 0.4 ml of water. The hydrolysed reaction mixture is treated with 1 g of activated charcoal and then filtered. The yellow filtrate is mixed with 20 ml of a 10% solution of diphenyldiazomethane in dichloromethane, and then concentrated to 10 ml in vacuo. The product is precipitated from the residue of evaporation thus obtained by adding 100 ml of n-hexane. 7-phenylacetamido-3-formyl-3-cephem-4-carboxylic acid benzhydrylester is thus obtained as a slightly yellowish product.

$^1$H-NMR (60 MHz, d$_6$-DMSO): 3.15 and 3.90 (AB$_q$, J=18 Hz, 2H, SCH$_2$); 3.55 (s, 2H, —CH$_2$—CO). 4.9 (d, J=5 Hz, 1H, H-6); 5.90 (dd, J=5 and 8 Hz, 1H, H-7); 6.6 (d, J=8 Hz, 1H, NH); 7.0 (s, 1H, CHPh$_2$); 7.25 and 7.30 (2s, 15H, Ar—H); 9.62 (s, 1H, CH=O).

21) 7-Amino-3-[[(aminocarbonyl)hydrazono]methyl]-3-cephem-4-carboxylic acid 1.3 g of semicarbazide-hydrochloride are dissolved in 30 ml of water and the solution is cooled to 0°. To this solution are added 3.0 g of the hydrochloride of 6-amino-1,4,5a,6-tetrahydro-3-hydroxy-1,7-dioxo-3H,7H-aceto[2,1-b]furo[3,4-d][1,3]thiazine in small portions. The reaction mixture is stirred at 3 to 5° for 4 hours. The precipitate which is 7-Amino-3-[[(aminocarbonyl)hydrazono]methyl]-3-cephem-4-arboxylic acid is filtered off and washed with 10 ml of acetone.

$^1$H-NMR (300 MHz, CD$_3$OD): 8.35 (s, 1H, CH=N); 5.31 (d, J=5.1 Hz, 1H, CH); 5.14 (d, J=5.1 Hz, 1H, CH); 4.28 und 3.84 (ABq, J=17.9 Hz, S—CH$_2$).

22) 7-Amino-3-(methoxyimino)methyl-3-cephem-4-carboxylic acid

A solution of 0.25 g of O-methylhydroxylamine-hydrochloride in 7 ml of water is mixed at 0° with 0.79 g of the hydrochloride of 6-amino-1,4,5a,6-tetrahydro-3-hydroxy-1,7-dioxo-3H,7H-aceto[2,1-b]furo[3,4-d][1,3] thiazine. After stirring for 15 hours at 0°, the suspention obtained is filtered. The crystal cake is washed with cold water and acetone. After drying in vacuo, 7-amino-3-(methoxyimino)methyl-3-cephem-4-carboxylic acid is obtained as an almost white, crystalline powder.

$^1$H-NMR (CD$_3$COOD+CF$_3$COOD): 3.99 (2H, S—CH$_2$): 4.01 (s, 3H, CH$_3$O); 5.39 (2H, β-lactam-H); 8.67 (s, 1H, CH=N). IR (KBr): 1799 cm$^{-1}$ (C=O, β-lactam).

23) 7-Amino-3[(E)-2-tert.butoxycarbonyl]ethenyl-3-cephem-4-carboxylic acid

A suspension of 1 g of 6-amino-1,4,5a,6-tetrahydro-3-hydroxy-1,7-dioxo-3H,7H-aceto[2,1-b]furo[3,4-d][1,3]thiazine in 10 ml of methylenchloride is treated at room temperature with 3.6 ml BSA. The reaction mixture is stirred for 10 minutes at room temperature. A clear solution is obtained containing N,O-bistrimethylsilyl-7-amino-3-formyl-3-cephem-4-carboxylic acid. The solution is cooled to 0° and treated with 0.37 g of lithium acetate and 1.5 ml of DMF. After 15 minutes whilst stirring under cooling in an ice bath 1.42 g tert.butoxy-carbonylmethylene-triphenylphosphorane are added After 24 hours stirring at 0° the reaction mixture is stirred into 30 ml of methanol. The product crystallizes. After 30 minutes stirring at room temperature the crystal suspension is filtered and the filter cake is washed with methanol. After drying 0.76 g (65.4%) of 7-amino-3[(E)-2-tert.butoxycarbonyl]ethenyl-3-cephem-4-carboxylic acid as a light coloured, crystalline powder are obtained.

IR-spectrum (KBr): 1803 cm$^{-1}$ (C=O β-lactam), 1705 cm$^{-1}$ (C=O ester); $^1$H-NMR-spectrum (90 MHz, D$_2$O+K$_2$CO$_3$): 1.50 (s, 9H, C(CH$_3$)$_3$); 3.61 (2H, S—CH$_2$); 4.82 (d, J=4.5 Hz, 1H, β-lactam-H); 5.31 (d, J=45 Hz, 1H, β-lactam-H); 5.97 (d, J=15.0 Hz, 1H, C=CH—CO); 7.65 (d, J=15.0 Hz, 1H, CH=C—CO).

24) 7-Amino-3[(E)-2-ethoxycarbonyl]ethenyl-3-cephem-4-carboxylic acid

A suspension of 1 g of 7-amino-3-formyl-3-cephem-4-carboxylic acid in 10 ml of propylene oxide is treated at room temperature with 4.7 ml of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated with 1.45 g of ethoxycarbonyl-methyltriphenylphosphonium chloride. After 44 hours stirring at 0° the reaction mixture is worked up as described in example 23). After drying 0.90 g (71.7%) of 7-amino-3[(E)-2-ethoxycarbonyl]ethenyl-3-cephem-4-carboxylic acid as a light coloured, crystalline powder are obtained.

IR-spectrum (KBr): 1801 cm$^{-1}$ (C=O β-lactam), 1709 cm$^{-1}$ (C=O ester); UV-spectrum (H$_2$O): $\lambda_{max}$=316.1 nm; $^1$H-NMR-spectrum (90 MHz, DMSO-d$_2$+CF$_3$COOD): 2.24 (t, J=7.0 Hz, 3H, CH$_3$); 3.90 (AB$_q$, J=18.0 Hz. 2H, S—CHO; 4.18 (q, J=7.0 Hz, 2H, O—CH$_2$—); 5.30 (d, J=5.0 Hz, 1H, β-lactam-H); 5.36 (d, J=5.0 Hz, 1H, β-lactam-H); 6.30 (d, J=16.0 Hz, 1H, C=CH—CO); 7.80 (d, J=16.0 Hz, 1H, CH=C—CO).

25) 7-Amino-3[(E)-2-ethoxycarbonyl]ethenyl-3-cephem-4-carboxylic acid

A suspension of 1 g of 7-amino-3-formyl-3-cephem-4-carboxylic acid in 10 ml of propylene oxide is treated at room temperature with 4.7 ml of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated with 1.32 g of ethoxycarbonyl-methyltriphenylphosphorane. After 24 hours stirring at 0° the reaction mixture is worked up as described in example 23).

IR-spectrum (KBr): 1803 cm$^{-1}$ (C=O β-lactam), 1736 cm$^{-1}$ (C=O ester) UV-spectrum (H$_2$O): $\lambda_{max}$=316.1 nm $^1$H-NMR, UV and IR spectra are identical with the spectra of exampel 23).

26) 7-Amino-3[(E)-2-ethoxycarbonyl]ethenyl-3-cephem-4-carboxylic acid

A suspension of 200 mg of 7-amino-3-formyl-3-cephem-4-carboxylic acid in 2 ml of THF is treated at room temperature with 1.08 ml of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated dropwise with a mixture of 197 mg of diethylethoxycarbonylmethylphosphonate and 98 mg of potassium tert.butylate in 2 ml of THF. After 18 hours stirring at 0° the reaction mixture is worked up as described in example 23). 39 mg (15.5%) of 7-amino-3[(E)-2-ethoxycarbonyl]ethenyl-3-cephem-4-carboxylic acid a s a brown coloured powder are thus obtained.

$^1$H-NMR, UV and IR spectra are identical with the spectra of exampel 23).

27) 7-Amino-3[(E)-2-N-diethylcarbamoyl]ethenyl-3-cephem-4-carboxylic acid

A suspension of 300 mg of 7-amino-3-formyl-3-cephem-4-carboxylic acid in 3 ml of propylene oxide is treated at room temperature with 1.4 ml of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated with 377 mg of N,N-diethylcarbamoylmethylenphosphorane. After 24 hours stirring at 0° the reaction mixture is worked up as described in example 23). 205 mg (49.8%) of 7-amino-3[(E)-2-N-diethylcarbamoyl]ethenyl-3-cephem-4-carboxylic acid as light yellowish coloured powder are thus obtained.

IR-spectrum (KBr): 1798 cm$^{-1}$ (C=O β-lactam), 1635 cm$^{-1}$ (C=O amide); UV-spectrum (H$_2$O): $\lambda_{max}$=315.7 nm; $^1$H-NMR-spectrum (90 MHz, DMSO-d$_6$+CF$_3$COOD): 1.03–1.33 (m, 6H, 2×CH$_3$); 3.60–3.66 (m, 4H, 2×N—CH$_2$—); 3.87 (AB$_q$, 2H, S—CH$_2$—); 5.10 (d, J=4.8 Hz, 1H, β-lactam-H); 5.31 (d, J=4.8 Hz, 1H, β-lactam-H); 6.67 (d, J=15.0 Hz, 1H, C=CH—CO); 7.88 (d, J=5.0 Hz, 1H, CH=C—CO).

28) 7-Amino-3-(2-phenyl)ethenyl-3-cephem-4-carboxylic acid

A suspension of 0.3 g of 7-amino-3-formyl-3-cephem-4-carboxylic acid in 3 ml of THF is treated at room temperature with 1.4 ml of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated with a solution of 0.53 g of phenylmethylene triphenylphosphorane in 4 ml of THF. After 24 hours stirring at 0° the reaction mixture is worked up as described in example 23). A mixture of the isomers (6 parts Z-isomer and 11 parts E-isomer) is obtained.

29) {6R-[3(E)α,7β(Z)]}-7-{[(2-amino-4-thiazolyl)(methoxyimino)acetyl]amino}-3-(3-ethoxy-3-oxo-1-propenyl)-8-oxo-5-thia-1-azabicyclo[3.2.0]oct-2-ene-4-carboxylic acid (=7-[(2-amino-4-thiazolyl)(methoxyimino)actyl]amino-3-(3-ethoxy-3-oxo-1-propenyl)-3-cephem-4-carboxylic acid)

0.34 g of triethylamine are added dropwise at 0° to a suspension of 0.5 g of 7-amino-3-[(E)-3-ethoxy-3-oxo-1-propenyl)-3-cephem-4-carboxylic acid and 0.67 g of (2-amino4 thiazolyl)(methoxyimino)acetic acid mercapto-benzthiazolyl ester in 5 ml ethanol. The reaction mixture is stirred for 5 hours at this temperature. A clear solution is obtained. The pH is adjusted to about 2.5 by dropwise addition of diluted hydrochloric acid. A precipitate is formed. After 1 hour stirring at 0° the crystal suspension is filtered and the filter cake is washed with ethanol. After drying 0.27 g (33.6%) of 7-[(2-amino-4-thiazolyl)(methoxyimino)actyl]amino-3-(3-ethoxy-3-oxo-1-propenyl)-3-cephem-4-carboxylic acid as a light coloured, crystalline powder are obtained.

$^1$H-NMR spectrum (90 MHz, DMSO-d$_5$): 1.22 (t, J=$^{7.0}$ Hz, 3H,—CH$_3$); 3.80 (AB$_q$, J=18 Hz, 2H, S—CH$_2$); 3.87 (s, 3H, O—CH$_3$); 4.18 (q, J=7.0 Hz, 2H, O—CH$_2$); 5.25 (d, J=4.8 Hz 1H, β-lactam H); 5.86 (dd, J=8.5 Hz, J=4.8 Hz, 1H, βlactam H); 6.24 (d, J=16.0 Hz, 1H, C=CH—CO); 7.73 (d, J=16.0 Hz, 1H, CH=C—CO); 9.70 (d, J=8.5 Hz, 1H.

30) 7-Amino-3[(E)-N-(2,2,2-trifluorethyl)pyrrolidine-2-on-3-ylidemethyl]-3-cephem-4-carboxylic acid A suspension of 126 mg of 7-amino-3-formyl-3-cephem-4-carboxylic acid in 2 ml of propylene oxide is treated at room temperature with 572 mg of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated with 152 mg of N-(2,2,2-muorethyl )-pyrrolidine-2-on-3-yl-triphenylphosphonium-bromide. After 24 hours stirring at 0° the reaction mixture is worked up as described in example 23). After drying 119 mg (57%) of 7-amino-3[(E)-N-(2,2,2-trifluormethyl)pyrrlidine-2-on-3-ylidenmethyl]-3-ephem-4-carboxylic acid as a light coloured, crystalline powder are thus obtained.

IR-spectrum (KBr): 1791 cm$^{-1}$ (C=O β-Lactam), 1692 cm$^{-1}$ (C=O Amid); UV-spectrum (H$_2$O): $\lambda_{max}$=324.3 nm; $^1$H-NMR-spetrum (90 MHz DMSO-d$_2$+CF$_3$COOD): 2.91–3.23 (m, 2H, C—CH$_2$—C-pyrrolidinon); 3.47–3.58 (m, 2H, N—CH$_2$-Pyrrolidinon); 3.99 (q, J=15 Hz, 2H, S—CH$_2$—); 4.17 (AB$_q$, J=15 Hz, N—CH$_2$—CF$_3$); 5.25 (d, J=3.0 Hz, 1H, β-lactam-H); 5.32 (d, J=3.0 Hz, 1H, β-lactam-H); 7.47 (t, J=3 Hz, 1H, CH=C).

31) 7-Amino-3[(E)-N-methylpyrrolidine-2-on-3-ylidenmethyl]-3-cephem-4-carboxylic acid.

A suspension of 300 mg of 7-amino-3-formyl-3-cephem-4-carboxylic acid in 3 ml of propylene oxide is treated at room temperature with 1.6 ml of BSA. The reaction mixture is stirred at room temperature for 10 minutes. A clear solution is obtained containing N,O-bistrimethylsilyl-7-amino-3-formyl-3-cephem-4-carboxylic acid. The solution is cooled to 0° and treated with 445 mg of N-methylpyrrolidine-2-on-3-yl-methylene triphenylphosphorane. After 15 hours stirring at 0° the reaction mixture is worked up as described in example 23). After drying 328 mg (83.9%) of 7-amino-3[E)-N-methylpyrrolidine-2-on-3-ylidenmethyl]-3-cephem-4-carboxylic acid as a light coloured powder are thus obtained.

IR-spectrum (KBr): 1783 cm$^{-1}$ (C=O β-lactam). $^1$H-NMR-spectrum (90 MHz, DMSO-$d_6$+CF$_3$COOD): 2.88 (s, 3H, N—CH$_3$); 2.80–356 (m, 4H, H-pyrrolidinon); 3.95 (ABq, J=19.3 Hz, 2H S—CH$_2$); 5.21 (d, J=5.7 Hz, 1H, β-lactam-H); 5.29 (d, J=5.7 Hz, 1H, β-lactam-H); 7.32 (t, J=3 Hz, 1H, CH=C).

We claim:

1. A compound of formula

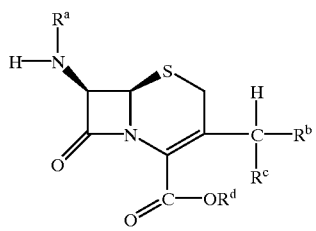

IA wherein $R^a$ denotes hydrogen or a silyl group;
$R^b$ denotes a group of formula —OR$^e$, wherein
$R^e$ denotes hydrogen or alkyl; and
$R^c$ and $R^d$ together denote a bond;
in free form or in salt form.

2. A compound according to claim 1 of formula

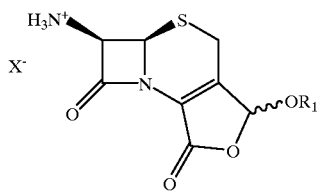

I wherein X$^-$ denotes the anion of an inorganic or organic acid and R$_1$ denotes hydrogen or an alkyl group.

3. A compound according to claim 2 wherein R$_1$ is C$_1$–C$_4$-alkyl.

4. A method of preparing a cephalosporin, which comprises preparing a compound of formula IA as an intermediate

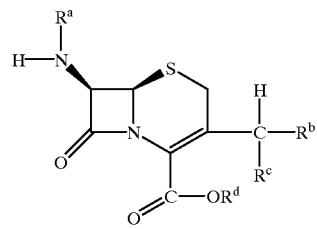

IA wherein $R^a$ denotes hydrogen or a silyl group;
$R^b$ denotes a group of formula —OR$^e$, wherein
$R^e$ denotes hydrogen or alkyl; and
$R^c$ and $R^d$ together denote a bond which forms a lactone ring;
in free form or in salt form.

5. A method of claim 4, wherein the compound of formula IA is modified by either
   (a) reacting the lactone ring formed by R$^c$, R$^d$ and R$^e$ with a nitrogen containing aldehyde reagent,
   (b) acylating the nitrogen attached to the ring system at the 7 position, or both of (a) and (b).

6. A method of claim 4, which comprises reacting the lactone ring formed by R$^c$, R$^d$ and R$^e$ with a nitrogen-containing aldehyde reagent.

7. A method of claim 5, wherein the nitrogen-containing aldehyde reagent is an amine, a hydroxylamine, a hydrazine, a guanidine or a semi-carbazide.

8. A method of claim 6, wherein the nitrogen-containing aldehyde reagent is an amine, a hydroxylamine, a hydrazine, a guanidine or a semi-carbazide.

9. A method of claim 4 which comprises acylating the nitrogen attached to the ring system at the 7 position.

10. A method of claim 4 wherein the compound of formula IA is a compound of formula

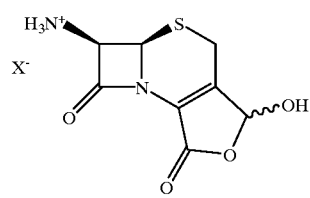

Ic wherein X$^-$ denotes the anion of an inorganic or organic acid and a compound of formula Ic is either
   i) reacted with a base, resulting in a compound of formula

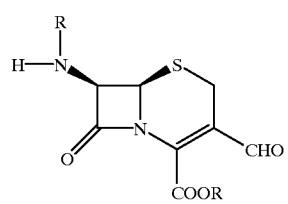

Ia wherein R denotes hydrogen, and reacting a compound of formula Ia with a silylation agent to obtain a compound of formula Ia wherein R denotes a silyl group; or ii) reacting a compound of formula Ic with a silylation agent, resulting in a compound of formula Ia wherein R denotes a silyl group; and reacting a compound of formula Ia wherein R denotes a silyl group with a compound of formula

XI

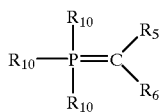

or with a compound of formula

XII

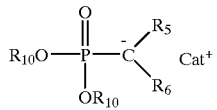

wherein $R_5$ and $R_6$ are the same or different and denote hydrogen or an organic group or $R_5$ and $R_6$ denote together a substituted or unsubstituted ring;

$R_{10}$ denotes aryl or lower alkyl and

Cat⁺ denotes a cation of an alkali metal or the protonated form of a strong organic base to give a compound of formula

XIII

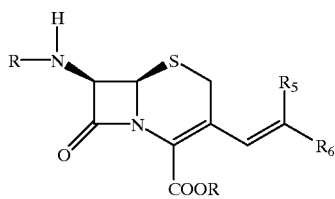

wherein R, $R_5$ and $R_6$ are as defined above.

11. A method of claim 10 which further comprises desilylating the compound of formula XIII to yield a compound of formula

VI

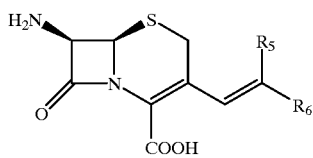

12. A method according to claim 11, comprising acylating the amine group in position 7 of the ring structure.

13. A method of preparing a cephalosporin according to claim 4, which comprises preparing a compound of formula I as an intermediate

I

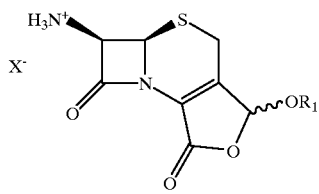

wherein X⁻ denotes the anion of an inorganic or organic acid and $R_1$ denotes hydrogen or an alkyl group.

14. A method of claim 13, wherein the compound of formula I is modified by either
(a) reacting the lactone group with a nitrogen containing aldehyde reagent,
(b) acylating the nitrogen attached to the ring system at the 7 position,
or both of (a) and (b).

15. A method of claim 13, which comprises reacting the lactone ring with a nitrogen-containing aldehyde reagent.

16. A method of claim 14, wherein the nitrogen-containing aldehyde reagent is an amine, a hydroxylamine, a hydrazine, a guanidine or a semi-carbazide.

17. A method of claim 15, wherein the nitrogen-containing aldehyde reagent is an amine, a hydroxylamine, a hydrazine, a guanidine or a semi-carbazide.

18. A method of claim 13 which comprises acylating the nitrogen attached to the ring system at the 7 position.

19. A method of claim 11, comprising acylating the amine group in position 7 of the ring structure in a compound of formula XIII or in a compound of formula VI.

20. An acid addition salt of 7-amino-3-formyl-3-cephem-4-carboxylic acid hydroxylactones (3H,7H-aceto[2,1-b]furo[3,4-d][1,3]thiazine-1,7(4H)-dione,6-amino-5a,6-dihydro-3-hydroxy-) or of 7-amino-3-formyl-3-cephem-4-carboxylic acid alkoxy-lactones (3H,7H-aceto[2,1-b]furo[3,4-d](1,3]thiazine-1,7(4H)-dione,6-amino-5a,6-dihydro-3-alkpxy-).

21. A compound selected from the group consisting of
3H,7H-aceto[2,1-b]furo[3,4-d][1,3]thiazine-1,7(4H)-dione,6-amino-5a,6-dihydro-3-hydroxyhydrochloride,
3H,7H-aceto[2,1-b]furo[3,4-d][1,3]thiazine-1,7(4H)-dione,6-amino-5a,6-dihydro-3-hydroxytoluenesulphonate,
3H,7H-aceto[2,1-b]furo[3,4-d][1,3]thiazine-1,7(4H)-dione,6-amino-5a,6-dihydro-3-methoxyhydrochloride and
3H,7H-aceto[2, 1-b]furo[3,4-d][1,3]thiazine-1,7(4H)-dione,6-amino-5a,6-dihydro-3-methoxy-toluenesulphonate.

22. A compound of formula

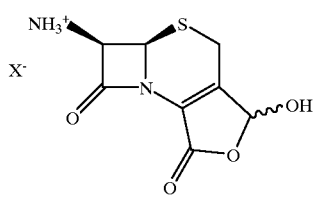

wherein $X^{-1}$ signifies the anion of an inorganic or organic acid.

* * * * *

UNITED STATES PATENT AND TRADEMARK OFFICE
CERTIFICATE OF CORRECTION

PATENT NO. : 6,093,813
DATED : July 25, 2000
INVENTOR(S) : ASCHER ET AL.

It is certified that error appears in the above-identified patent and that said Letters Patent is hereby corrected as shown below:

COLUMN 32

Line 40, "thiazine-1,7(4H)-dione,6-amino-5a,6-dihydro-3-alkpxy-)." should read
-- thiazine-1,7(4H)-dione,6-amino-5a,6-dihydro-3-alkoxy-). --

Line 65, "$X^{-1}$" should read -- $X^-$ --.

Signed and Sealed this

Seventeenth Day of April, 2001

Attest:

NICHOLAS P. GODICI

*Attesting Officer*        *Acting Director of the United States Patent and Trademark Office*